United States Patent [19]

Kenna et al.

[11] Patent Number: 4,646,729
[45] Date of Patent: Mar. 3, 1987

[54] PROSTHETIC KNEE IMPLANTATION

[75] Inventors: Robert V. Kenna, Saddle River, N.J.; David S. Hungerford, Cockeysville; Kenneth A. Krackow, Baltimore, both of Md.

[73] Assignee: Howmedica, Inc., Wilmington, Del.

[21] Appl. No.: 811,020

[22] Filed: Dec. 19, 1985

[51] Int. Cl.⁴ .............................................. A61F 5/04
[52] U.S. Cl. .......................... 128/92 VW; 128/92 VD; 128/92 VL
[58] Field of Search ............. 128/1 R, 303, 305, 92 E, 128/92 EB, 92 C, 92 H

[56] References Cited

U.S. PATENT DOCUMENTS 4,211,228  9/1980  Cloutier ........................... 128/303 R

OTHER PUBLICATIONS

David S. Hungerford, M. D., Kenneth A. Krackow, M. D., Robert V. Kenna, The Howmedica, "Universal Total Knee Instrument System", 1981.

Nas. S. Eftekhar, M. D., "Total Knee-Replacement Arthroplasty", Journal of Bone and Joint Surgery, vol. 65-A, No. 3, Mar. 1983, pp. 283-309.

*Primary Examiner*—Stephen C. Pellegrino
*Attorney, Agent, or Firm*—Harold Pezzner

[57] ABSTRACT

A prosthetic knee is implanted after cutting the femor and tibia in the proper manner with the aid of instruments which include axial alignment guides and a series of cutting jigs.

8 Claims, 101 Drawing Figures

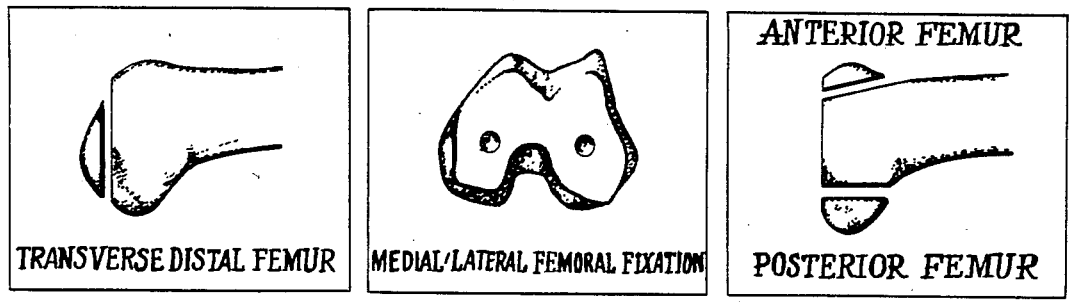
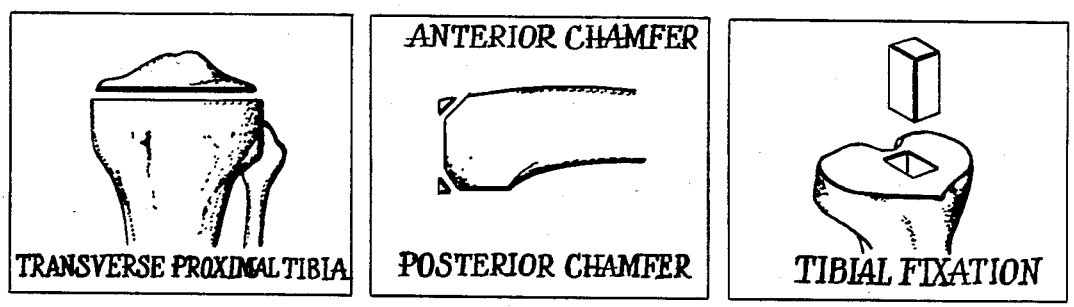
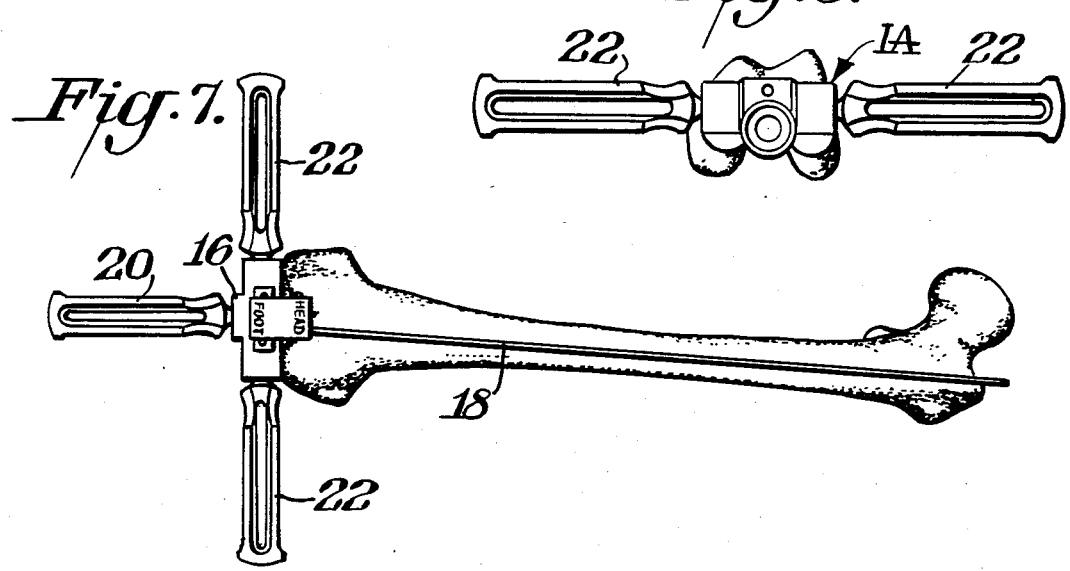

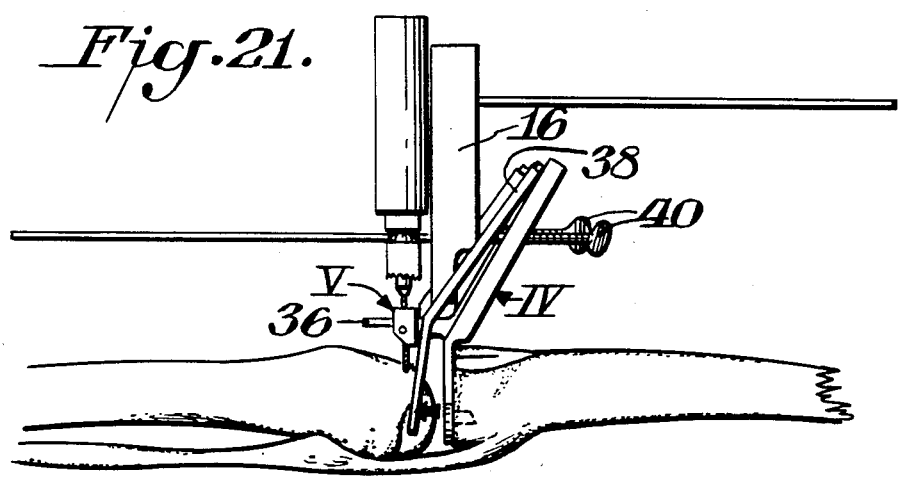
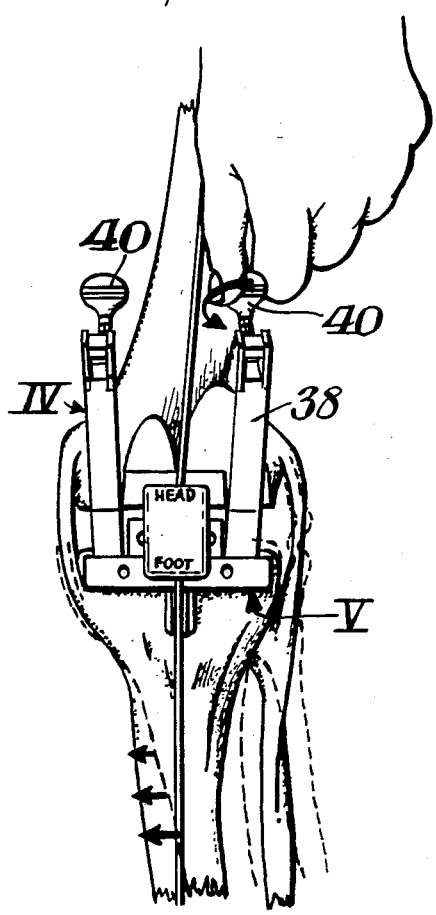
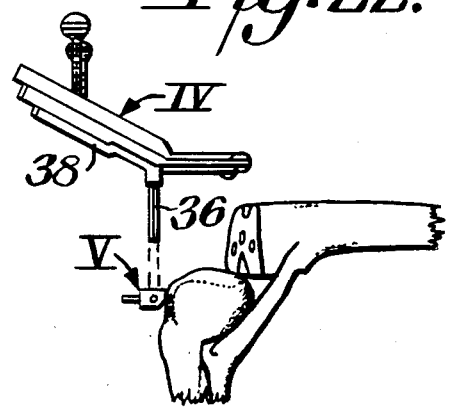
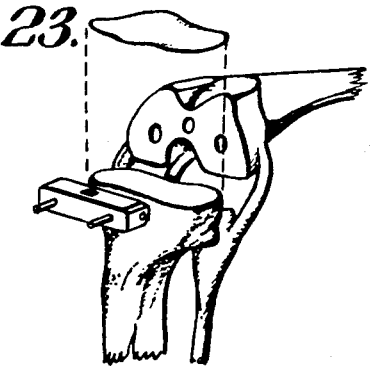
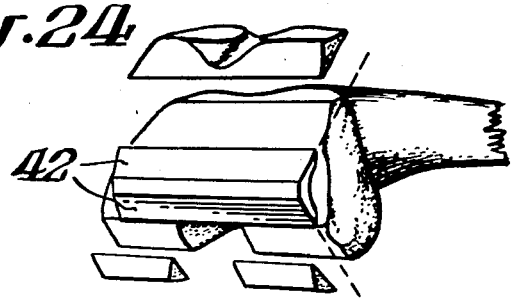

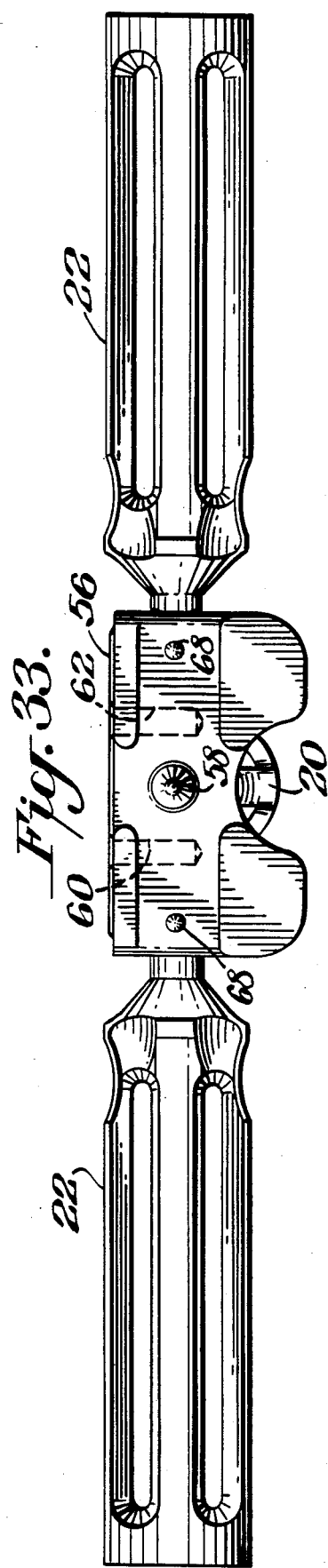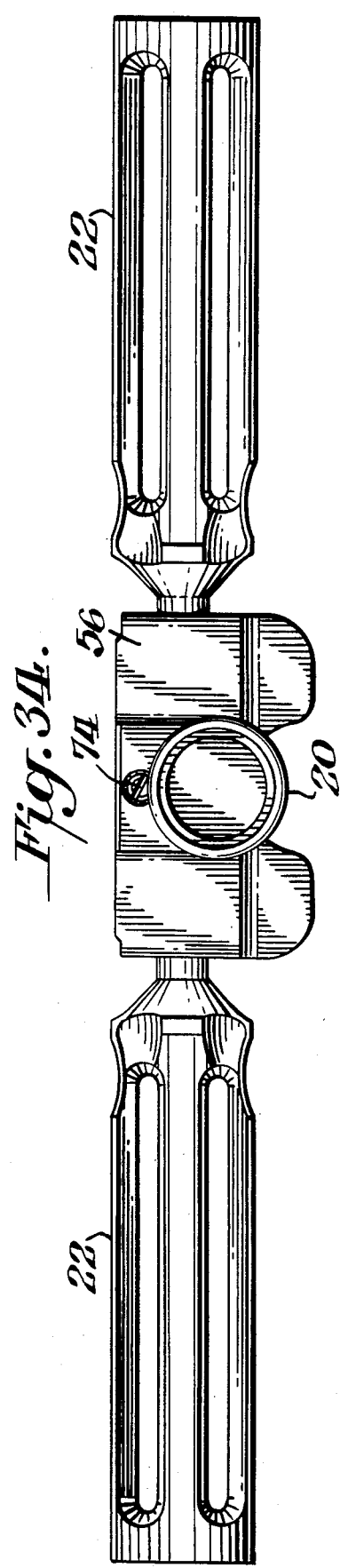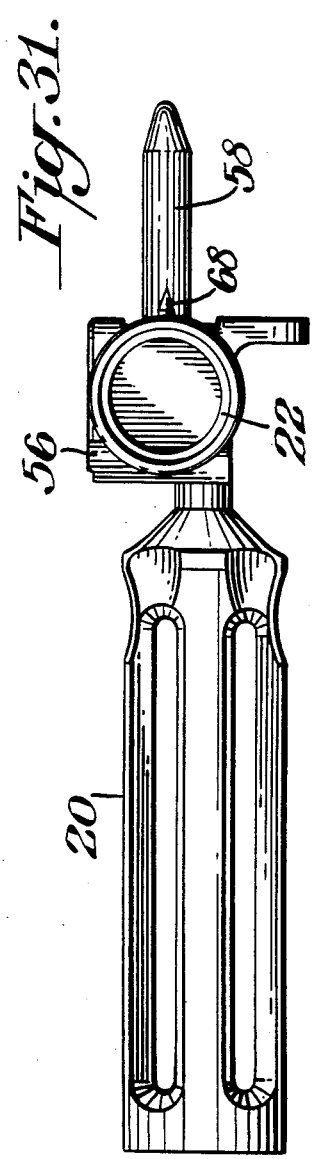

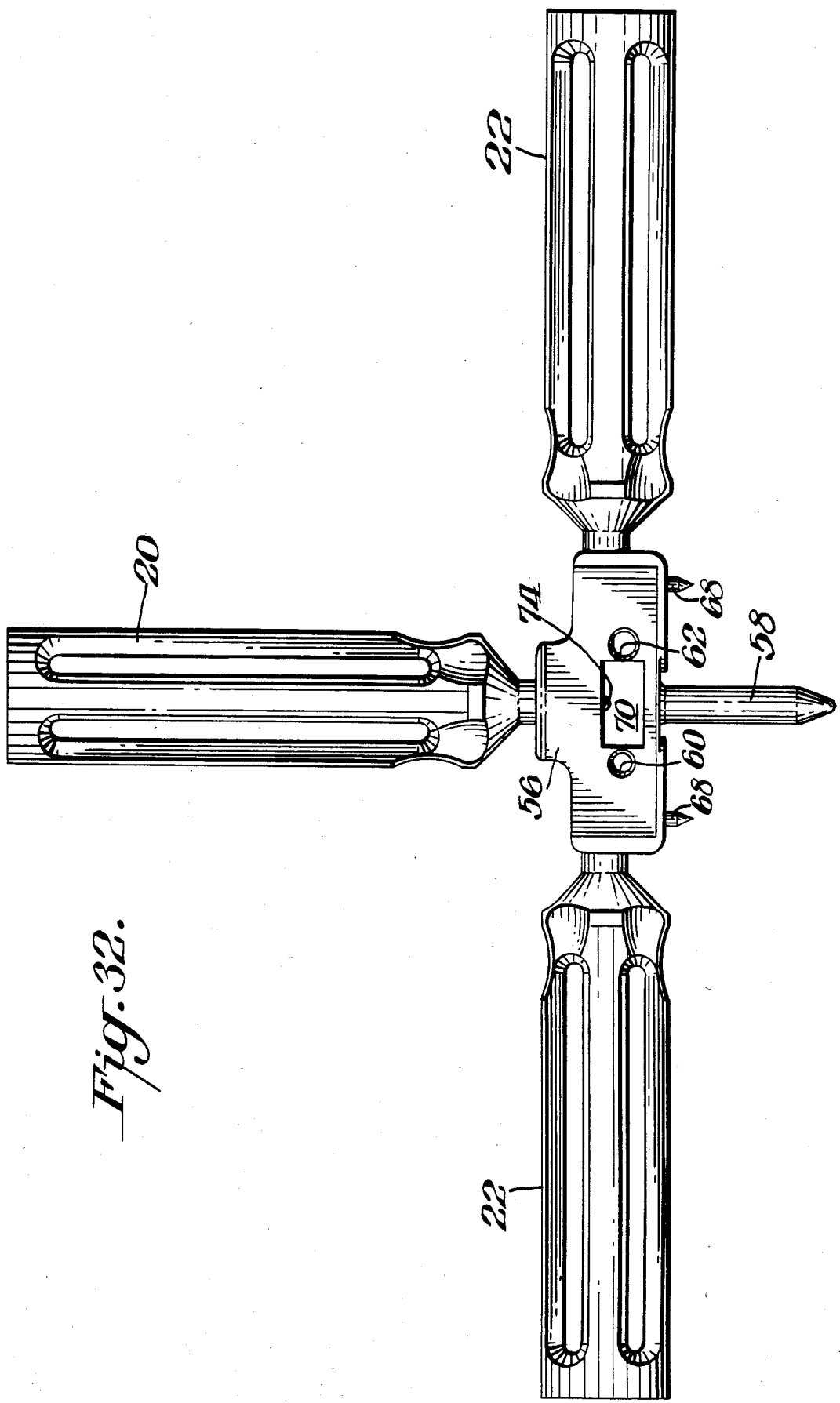

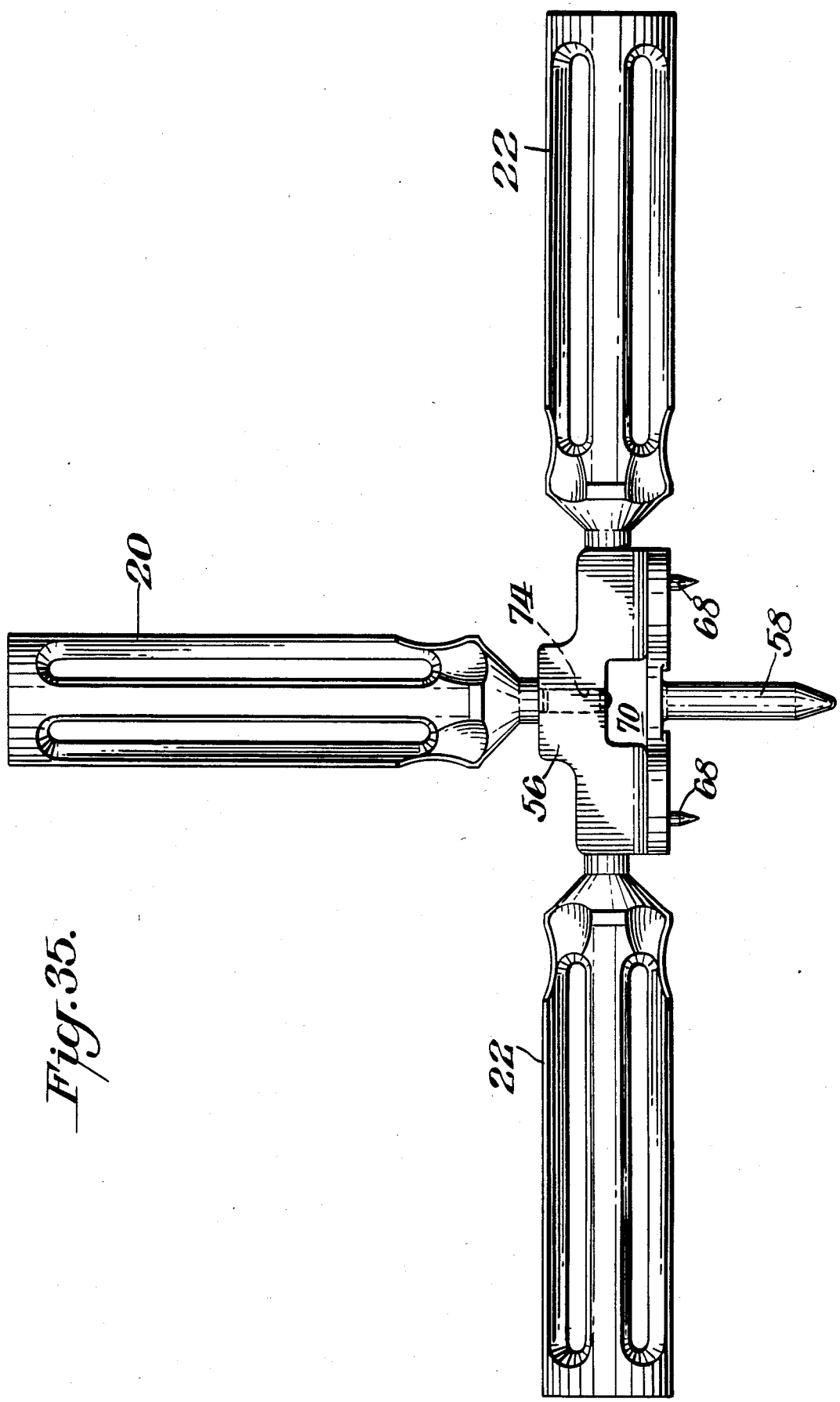

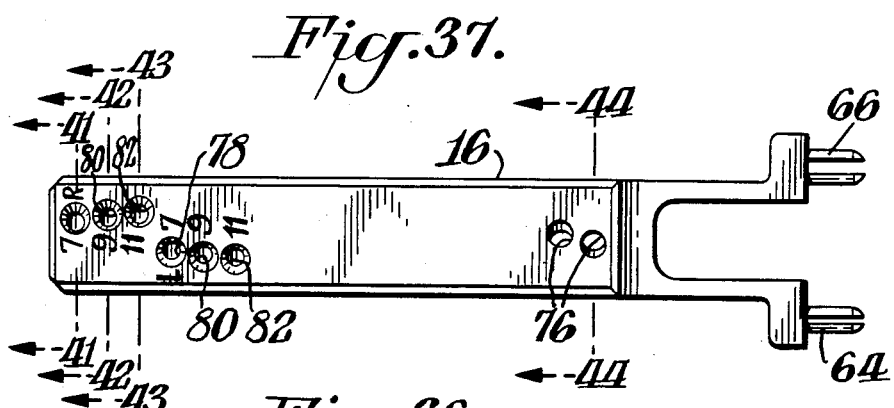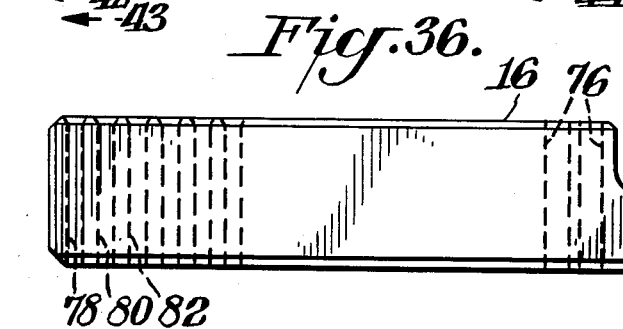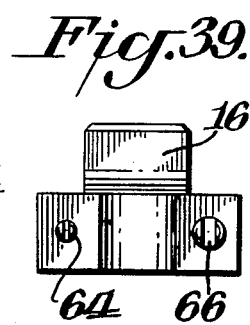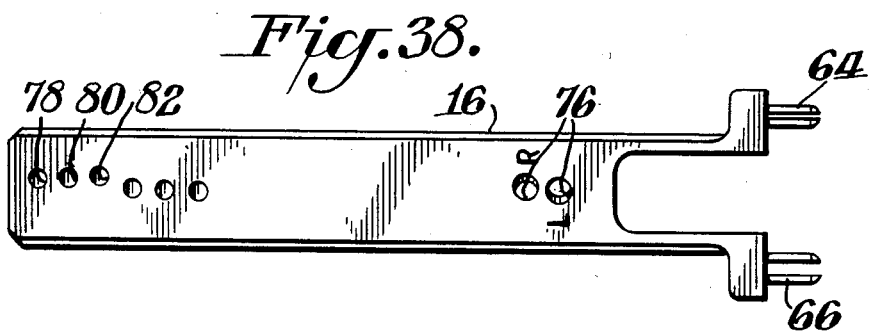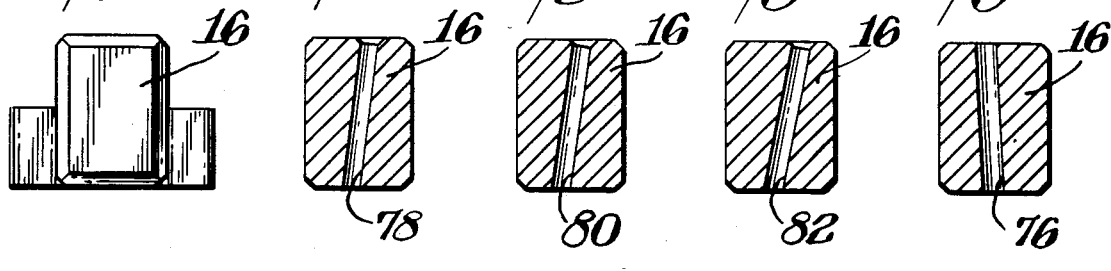

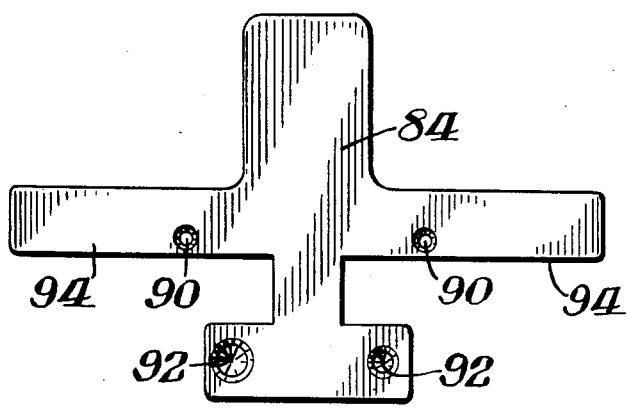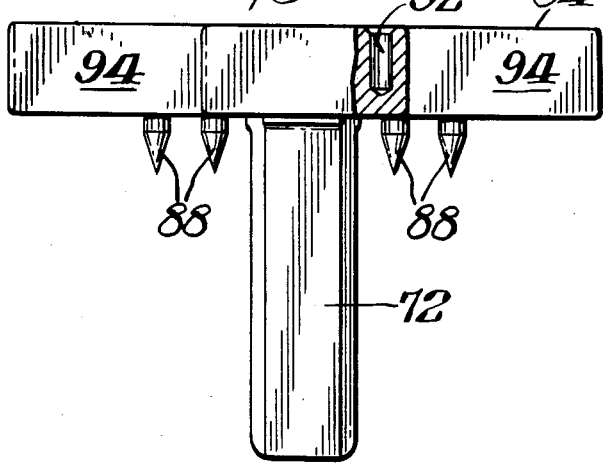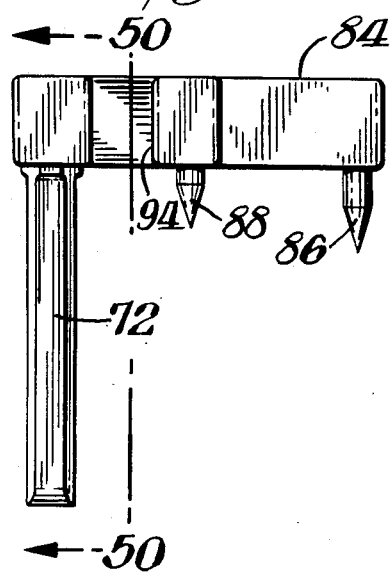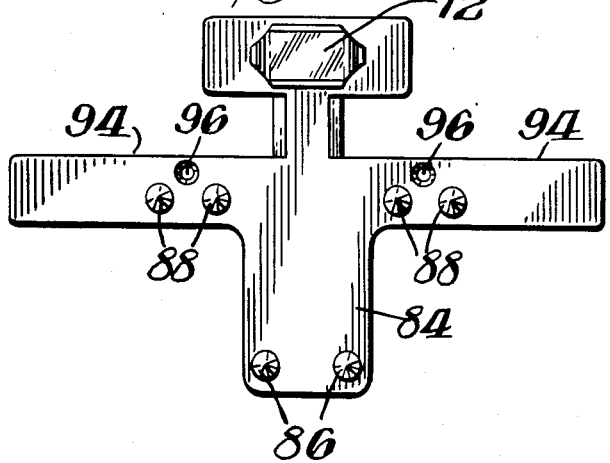

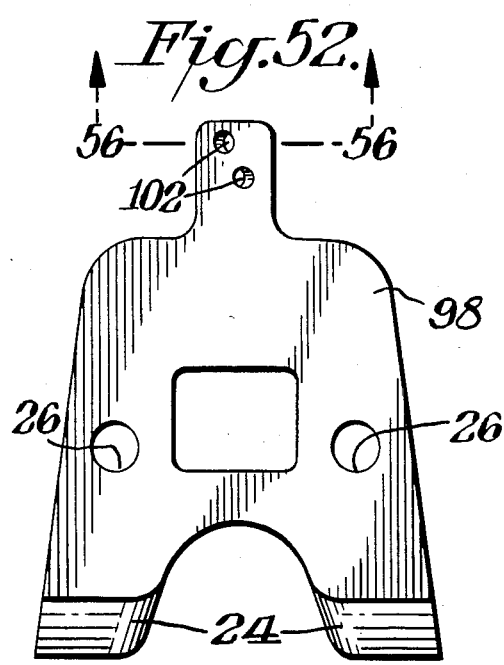
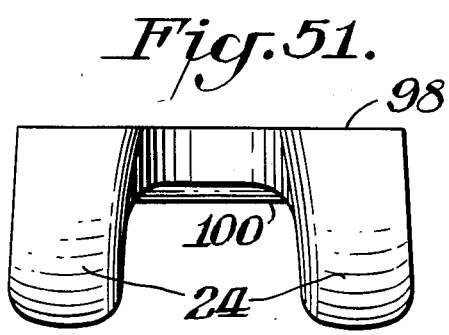
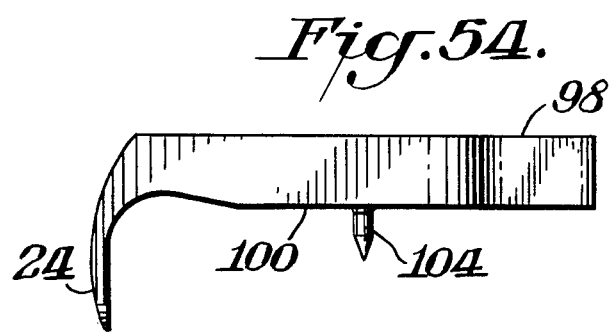
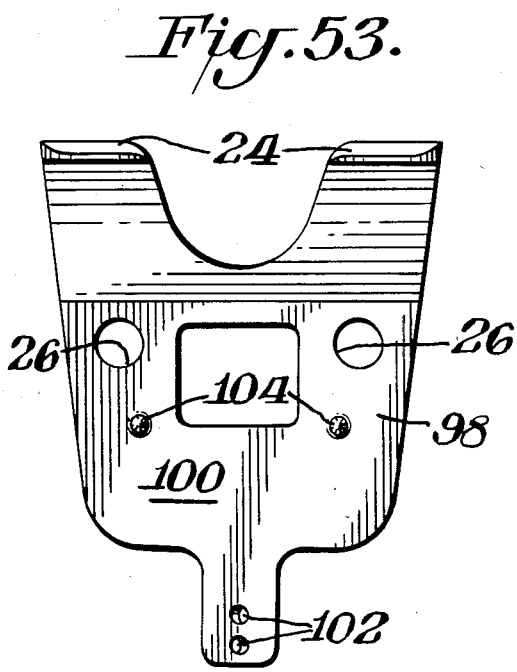
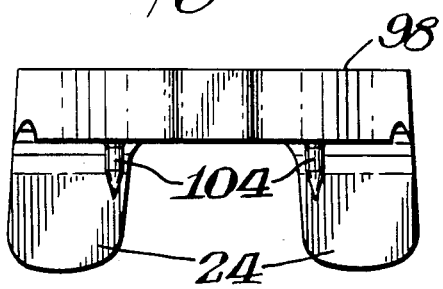

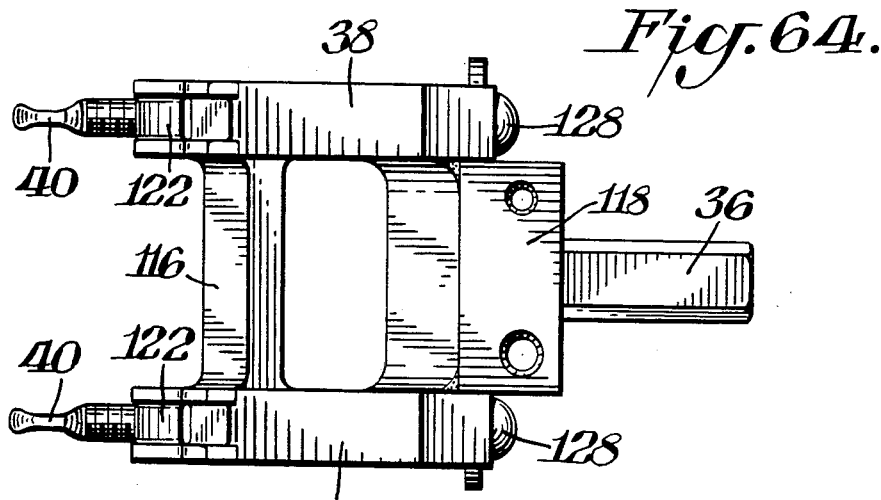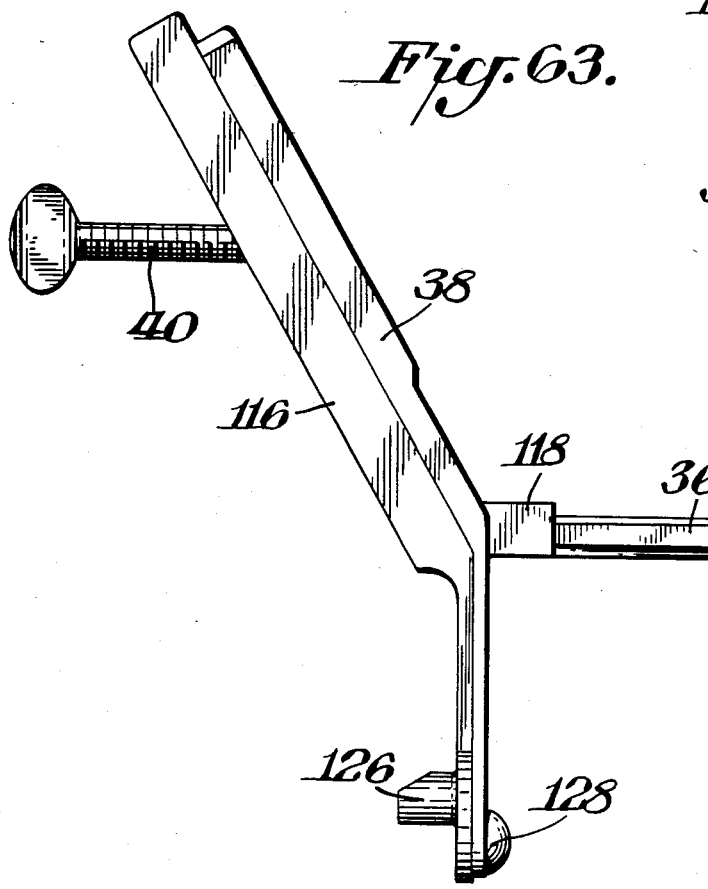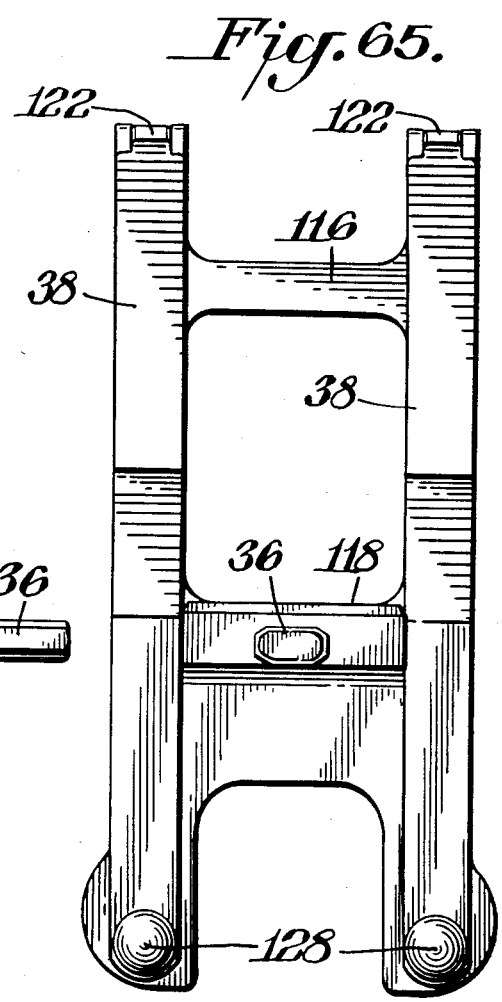

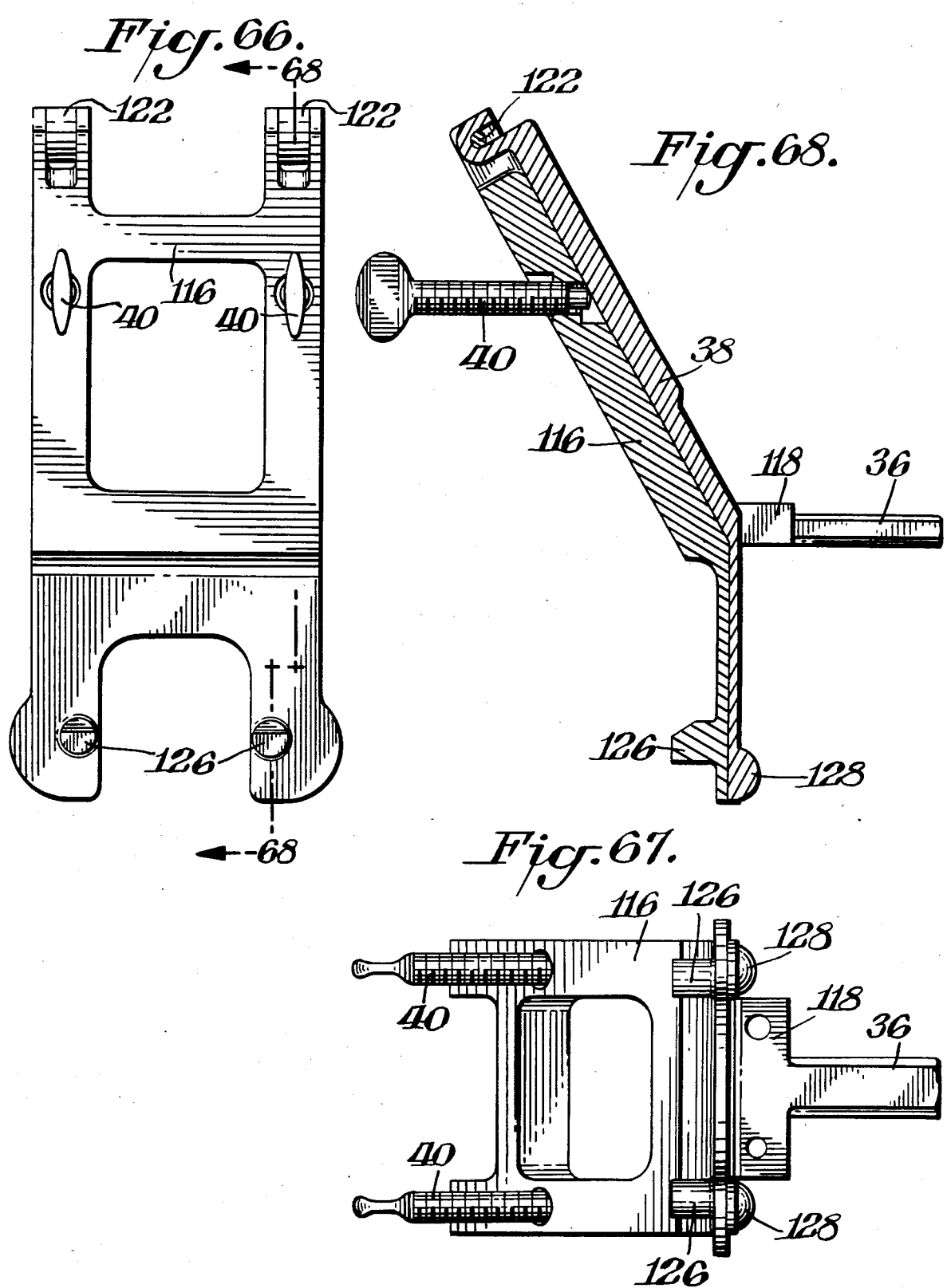

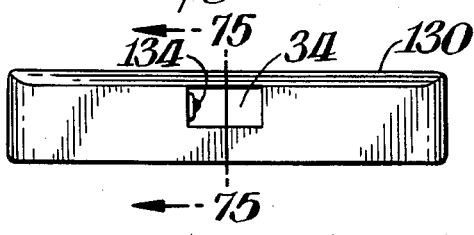
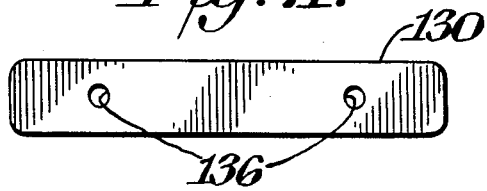
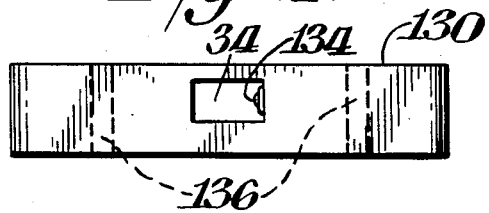
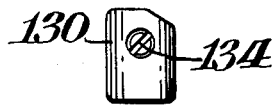
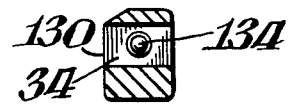

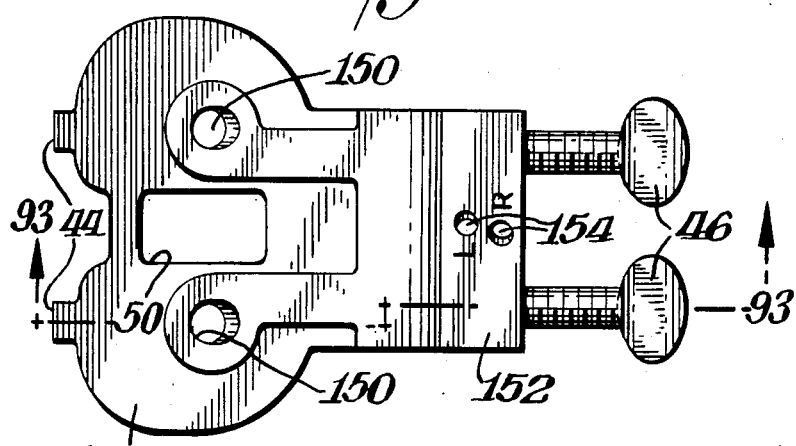
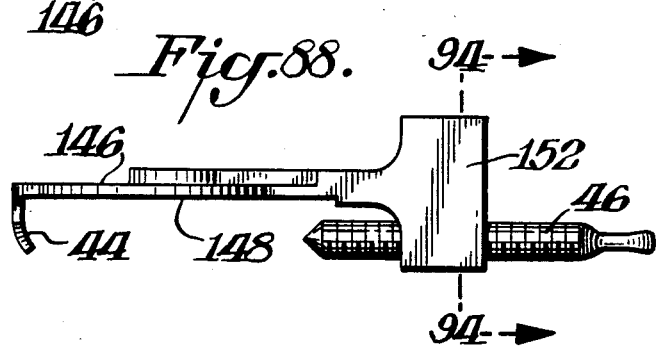
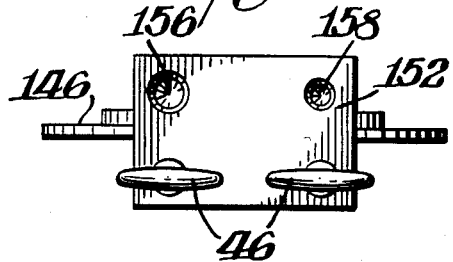
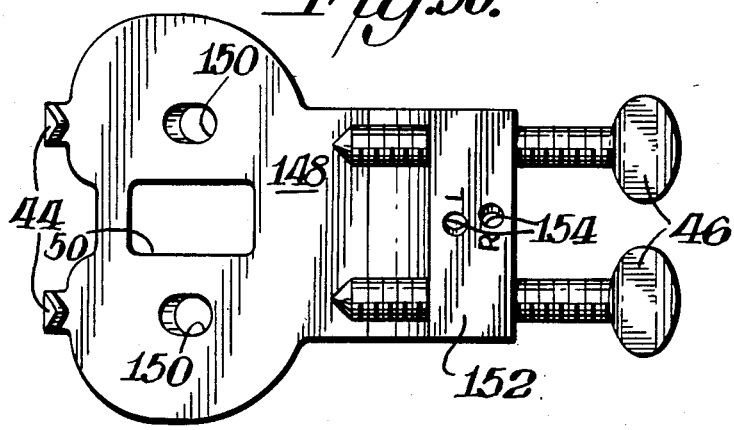
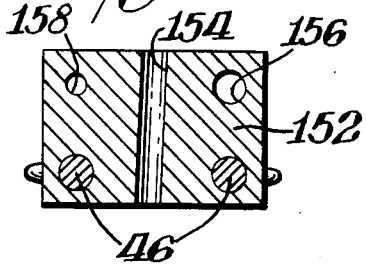
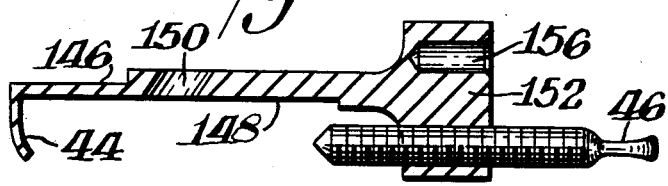
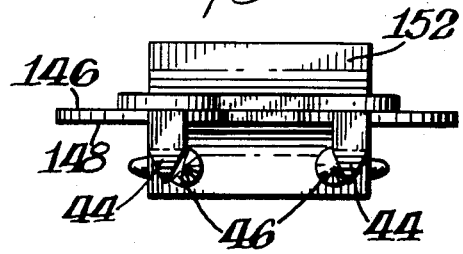

PROSTHETIC KNEE IMPLANTATION

BACKGROUND OF THE INVENTION

Prosthetic knee components have long been known and used in the art. In order to prepare the femor and tibia for the components, it is necessary to make a series of cuts from these bones to conform to the size and shape of the prosthetic components. Generally these cuts are made by visual reliance on where the cuts should be sometimes with the aid of simplified jigs and/or score lines. Such techniques are necessarily imprecise which limits the ability to provide the anatomically most desirable prosthetic knee.

Applicant's copending application, filed February 1982, the details of which are incorporated herein by reference thereto, describes such an anatomically desirable prosthetic knee system.

The aforenoted prosthesis is designed to reproduce anatomic movement of the knee without compromising stability. This prosthetic knee, as the natural knee, provides a "screw home" mechanism which increases stability in extension. As flexion proceeds, the femoral condyles initially roll posteriorly. Through asymmetric condylar and tibial compartments, the natural and changing axes of rotation are preserved, thereby preventing the development of abnormal tension in retained ligaments. When abnormal ligamentous tension develops, it either restricts flexion and increases shear stress at fixation interfaces and/or leads to eventual progressive ligament attenuation and joint instability. The design also allows natural internal and external rotation of the knee in flexion. Furthermore, contouring of the posterior margins of the tibial plateaus facilitates stability in flexion and provides a broad contact surface. The combination of these factors, which balance soft tissue elements in the joint, minimizes shear stress at the fixation interfaces, enhancing the potential for long term function of the replaced knee.

In order to make such prosthetic knee system feasible, the necessary bone cuts must be precisely accomplished. This, in turn, requires a set of proper instruments including guides and jigs. Such instruments should assure reproducibly accurate bone cuts, prosthetic seating, and lower limb alignment.

SUMMARY OF THE INVENTION

An object of this invention is to provide techniques which permit the above-noted knee prosthesis to be implanted.

A further object of this invention is to provide instruments including guides and cutting jigs which assure the necessary accurate bone cuts.

In accordance with this invention, a set of instruments is provided which allows for variations in the anatomical axis of the femor. The instruments include cutting jigs which are selectively locked directly to the bone. By use of these instruments, eight basis cone cuts are made to align and seat the femoral and tibial components of the prosthesis.

THE DRAWINGS

FIGS. 2a through 2f illustrate the eight basis bone cuts which are made in accordance with the invention;

FIGS. 3-30 illustrate the various steps and instruments used therein from incision to final tibial preparation in the practice of the invention;

FIGS. 31-35 are side, top, front, bottom and rear views, respectively, of the distal femoral cutting jig shown in FIGS. 7-13;

FIGS. 36-40 are side, front, rear, bottom and plan views, respectively, of the pin holder alignment guide shown in FIGS. 8-9;

FIGS. 41-44 are cross-sectional views taken through FIG. 37 along the lines 41—41, 42—42, 43—43 and 44—44;

FIG. 45 is a front elevation view partly in section of the distal femoral cutting jig shown in FIGS. 10-13;

FIGS. 46-49 are top, bottom, side and rear views, respectively, of the femoral cutting jig shown in FIG. 45;

FIGS. 51-55 are bottom, front, rear, side and top views, respectively, of the femoral drill jig shown in FIGS. 13-14;

FIG. 56 is a cross-sectional view taken through FIG. 52 along the line 56—56;

FIGS. 63-67 are side, top, front, rear and bottom views, respectively, of the femoral spacer/tensor jig shown in FIGS. 17-22;

FIG. 68 is a cross-sectional view taken through FIG. 66 along the line 68—68;

FIGS. 69-72 are top, rear, front and bottom elevation views, respectively, of the transverse tibial cutting jig shown in FIGS. 17-23;

FIGS. 73-74 are end elevation views of the transverse tibial cutting jig shown in FIGS. 29-72;

FIG. 75 is a cross-sectional view taken through FIG. 69 along the line 75—75;

FIGS. 88-92 are side, top, bottom, front and rear views, respectively, of the tibial positioning/fixation jig shown in FIGS. 25-30;

FIG. 93 is a cross-sectional view taken through FIG. 89 along the line 93—93; and FIG. 94 is a cross-sectional view taken through FIG. 88 along the line 94—94.

DETAILED DESCRIPTION

The instruments utilized in the practice of the invention consist of long axial alignment guides and cutting jigs. The jigs may be sequentially numbered relative to their order of use to simplify the procedure. The alignment guides are designed to assist the surgeon in positioning all primary cutting jigs prior to making the bone cuts. All cutting jigs lock onto their respective bones to insure the accuracy of the cuts.

The inventive instrument system is designed to seat the femoral and tibial components parallel to the anatomic transverse axis of the knee. Since this axis is parallel to the ground and perpendicular to the vertical in two-legged stance, this positioning achieves: (1) uniform stress distribution at fixation interfaces, (2) optimal alignment; and (3) physiological ligamentous balance of the knee. It is also important to recognize that the ankles remain closer to the midline vertical axis of the body that either the knees or hips throughout noral gait. To achieve the goals of total knee arthroplasty, these alignment features must be preserved or reconstituted.

Figure 1:
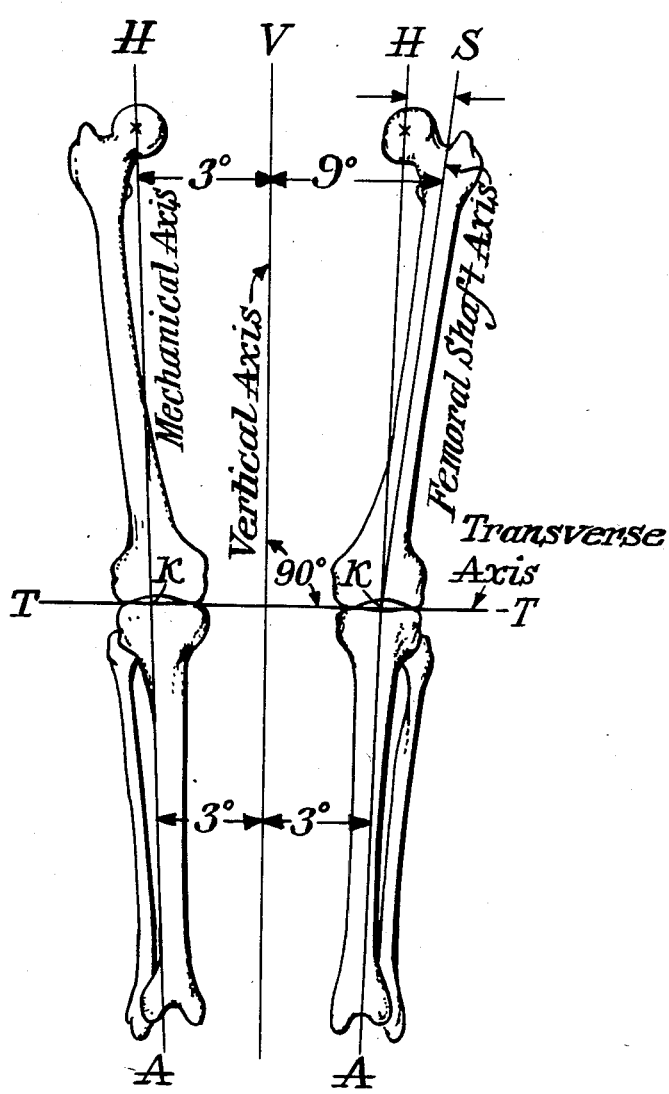
FIG. 1 illustrates the anatomical considerations of the legs which are taken into account in accordance with the invention.

The inventive instrument system uses the femoral shaft axis (S), the center of the knee (K), the center of the ankle joint (A), and the transverse axis of the knee (T) as its alignment references (FIG. 1). The mechanical axis of the lower libm, which runs from the center of the hip (H) thorugh the center of the knee (K) to the center of the ankle (A), generally forms an angle of 3° with the vertical (V), because the hips are wider apart than the ankles in both normal stance and gait (FIG. 1).

Since the femoral head and neck overhang the shaft, the axis of the femoral shaft does not coincide with that of the leg, but forms with the leg a more acute valgus angle of 6° (SKH, FIG. 1). In total, the femoral shaft axis averages 9° of valgus with the vertical. The valgus angle of the femur varies relative to body build. The specific femoral valgus for a given individual can be determined by measuring angle HKS (FIG. 1) on a long X-ray which includes both the hip and the knee, and adding 3° (the mechanical axis). This method is valid for reconstituting a mechanical axis of 3° regardless of the degree of pre-operative axial deformity at the knee.

For tibial alignment, the center of the knee and the center of the ankle are used as reference points. Instruments which rely on the proximal tibial shaft as their key alignment reference tend to be inaccurate due to the frequent occurrence of tibial bowing. Recognizing that the center of the ankle is closer to the midline vertical axis than the center of the knee in two-legged stance and throughout gait, this system uniquely requires a small angle at the proximal transverse tibal cut (TKA, FIG. 1). This angle keeps the transverse axis of the prosthesis parallel to the ground while the mechanical axis of the entire lower extremity remains in valgus (HKA, FIG. 1).

FIG. 2 illustrates the eight basic bone cuts required to align and seat the femoral and tibial components of the prosthesis. As later described in detail, the instrument system consists of seven sequentially numbered cutting jigs and a femoral/tibial alignment guide. These are designed to insure the accuracy and alignment of all femoral and tibial bone cuts.

Figure 3:
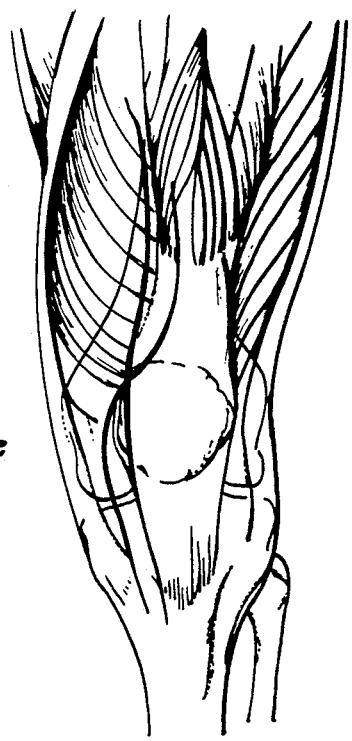

In the practice of the invention, the knee is approached through a longitudinal skin incision, followed by a medical parapatellar capsular incision. The quadriceps tendon is incised longitudinally, allowing eversion and dislocation of the patella laterally (FIG. 3).

Orientation

Figure 4:
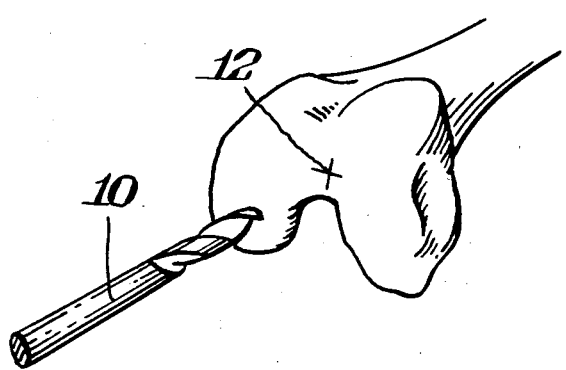
Figure 6:
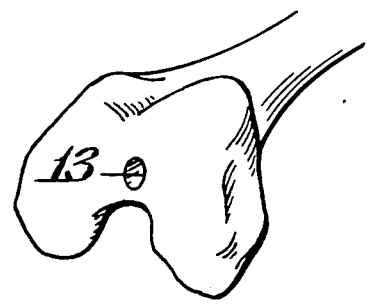

With the knee flexed to 90°, a 5/16 inch drill hole is made by drill bit 10 in the distal femur. It is placed roughly in the center 12 of the intercondylar notch just anterior to the femoral attachment of the posterior cruciate ligament (FIG. 4). The position of this hole 13 (FIG. 6) is not critical to the orientation of any femoral bone cuts—it is simply a point of purchase for the distal femoral cutting jig IA. The laterally protruding handles 22 are used to rotate the jig so that the posterior rounded eminences parallel to the posterior femoral condyles and the anterior femur is seen as on a sunrise view (FIG. 5). The jig is then hammered into place. Jig IA includes a pair of locking pins on the side hidden from view in FIG. 5. If there has been significant preoperative deformity, the short locking pin facing the most prominent condyle is hammered into place bringing the face of the jig IA flush to that condyle only.

Figure 9:
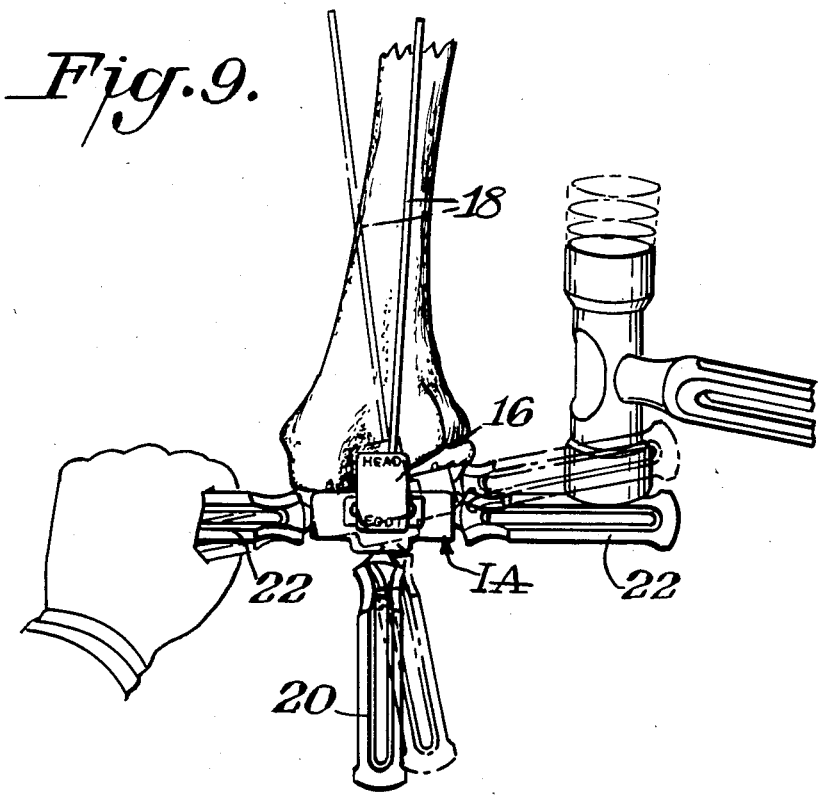

The Transverse Distal Femoral Cut: Varus-Valgus And Flexion-Extension Alignment The long axial alignment guide 16 is used to establish proper varus-valgus and flexion extension alignment of the distal femoral cuts. The guide pin 18 is positioned into the pin holder in the appropriate right or left 7°, 9° or 11° hole 20 (FIG. 37). This angle is chosen relative to the pre-operative X-ray measurement technique previously described in the alignment rationale section. Most often 9° will be appropriate. The guide 16 is then placed into the anterior holes of the distal femoral cutting jig IA. Correct axial alignment is achieved when the long alignment guide pin 18 is parallel to the femoral shaft axis in both the anterior and lateral views (FIGS. 7 and 8). An examining finger can be slipped proximally under the quadriceps to get a better idea of the direction of the femoral shaft during this alignment procedure. If the alignment pin 18 does not parallel the femoral shaft, a mallet is used to tap the medial handle 20 or lateral handle 22, advancing the jig IA away from the deformed condyle until the axial guide pin 18 parallels the femoral shaft (FIG. 9). With the alignment completed, one can easily visualize how much bone is missing from the deformed condyle. The IA jig is not stable at this point but must be manually held during insertion and removal of the alignment pinholder and also while placing the IB jig.

A short alignment pin is available to facilitate alignment in two special circumstances. The shorter pin avoids impingement with the tourniquet on an obese thigh or with the abdomen of a short patient.

Locking The Distal Femoral Cutting Jig In Position

Figure 10:
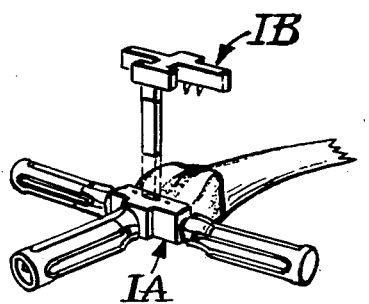
Figure 11:
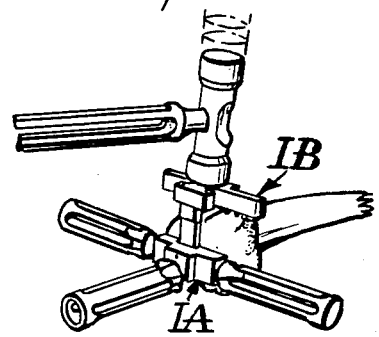

The axial alignment guide 16 is removed and the tongue of the distal femoral cutting jig IA and jig IB is slid into the first part of the distal femoral jig IA (FIG. 10). With the teeth of the IB jig resting lightly on the anterior femur, recheck the alignment for both varus-valgus and flexion-extension prior to hammering it in place. When proper alignment is assured, first gently tap the IB jig with a mallet so that the teeth engage the bone without sliding down an oblique surface, thereby changing alignment. Then remove the alignment guide and hammer the IB jig firmly in place. There are also drill holes in the cutting bar of the IB jig through which ⅛ inch drill pins can be passed into the condyles if additional stability is necessary.

Figure 12:
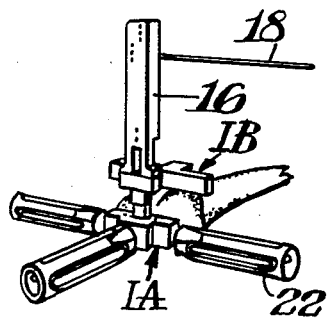

Final position of the distal femoral cutting jig IA is rechecked with the alignment guide. Measure twice, cut once (FIG. 12).

Cutting The Distal Femur

Figure 13:
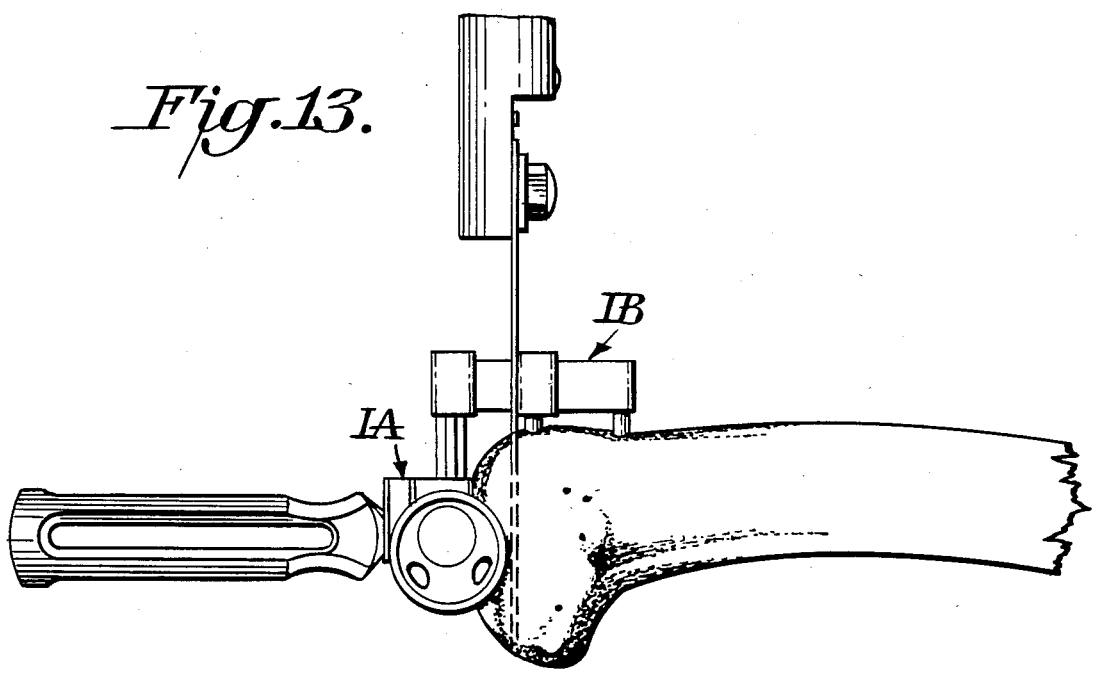

Once the distal femoral cutting jig IA is locked on to the femur, the surgeon is free to direct his full attention to the cutting of the distal condyles. Pistol grip, endcutting oscillating saws are most effective for these cuts. It is important that the surgeon pay strict attention to maintaining the saw blade flat against the proximal cutting surface of the jig in order to achieve a precise cut (FIG. 13). Care should be taken to avoid the central intramedullary fixation peg of the jig. Following the initial transverse cut, the saw blade is passed back and forth across the cutting bar to shave the condylar cuts level with the plane of the cutting jig. This step is important since the saw blade tends to scive away from the desired plane, particularly in more sclerotic bone and toward the deeper portions of the cut. The jigs are now removed and the distal femoral cuts are completed. In completing these cuts, the anterior aspect of the distal femoral cut will serve as the "cutting block" for the remaining posterior aspect. It is, therefore, important that the saw blade be inserted to the full depth of the initial cut before the oscillation is started. Otherwise, one runs the risk of starting a new plane. Once the posterior part has been completed, the broadest blade should be passed over the surface to be sure that the cut is a single-flat plane. This can also be checked with a cutting block.

Figure 14:
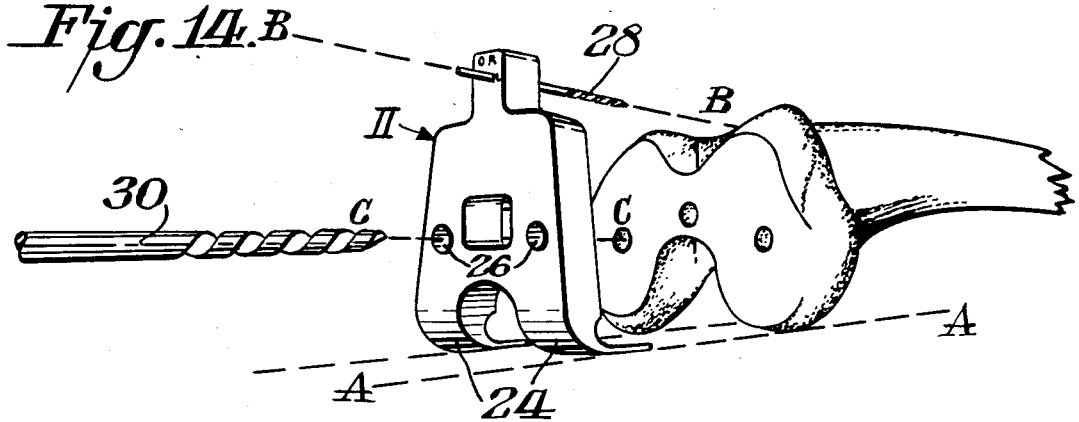

Femoral Corponent Rotational, Medial-Lateral And Anterior-Posterior Alignment Rotational, medial-lateral and anterior-posterior orientation of the femoral prosthesis is determined by the femoral drill jig II. This jig has two posterior skids 24 which are slid between the posterior femoral condyles and tibial plateaus. These skids automatically position the instrument in 0° of rotation relative to the coronal plane of the distal femur (A,A, FIG. 14). The jig should first be centered in the medial-lateral position on the flat cut distal femoral surface, ignoring the initial keying hole for the IA jig. The jig II is now hammered flush with the flat surface of the distal femoral condyles. The jig's anterior projection contains two holes 26 marked respectively for right and left knees. When a ⅛ inch drill pin 28, placed in the appropriate hole, is aligned with the center of the patello-femoral groove, correct medial-lateral and rotational positioning is assured (B,B, FIG. 14). When correct positioning has been assured, a 5/16 inch drill 30 is used to make the holes for the femoral prosthesis fixation studs (C,C, FIG. 14).

Anterior And Posterior Femoral Cuts

Figure 15:
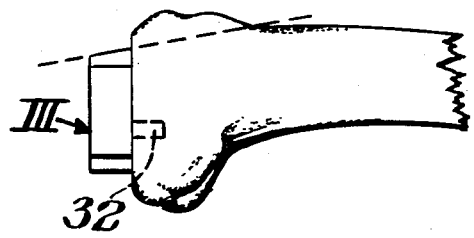
Figure 16:
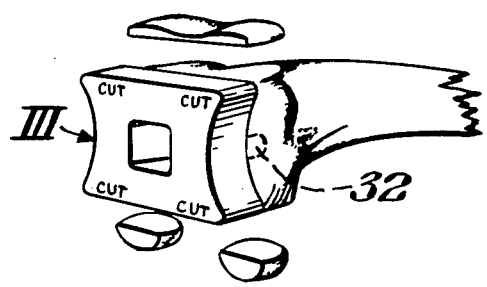

Following the removal of the drill jig II, the two 5/16 inch locking studs 32 of the anterior-posterior femoral cutting jig III, are inserted into the distal femoral fixation holes. The jig III is hammered flush with the flat cut surface of the distal femoral condyles. The anterior plane of the cutting jig should intersect the anterior cortex of the femur at the proximal margin of the patellar facets (FIG. 15). If this plane appears too deep or too anterior, the next most appropriate size jig should be chosen. If there is any question of which size jig is to be used, always start with the larger jig. The anterior and posterior femoral bone cuts are now completed (FIG. 16). Once again, care must be taken to rest the saw blade flush against the flat surface of the jig. With the posterior condyles removed, complete access to the posterior compartment allows removal of the menisci and anterior cruciate ligament. The tibial attachment of the posterior cruciate is identified and carefully avoided during the next step. Also, all remaining marginal osteophytes on the tibia and femur must be removed so they do not shorten or constrict ligaments or block full extension.

Tibial Alignment And Cuts

Figure 17:
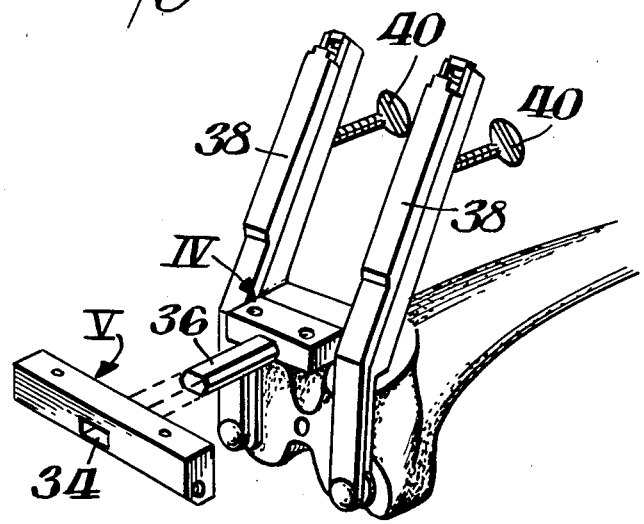
Figure 18:
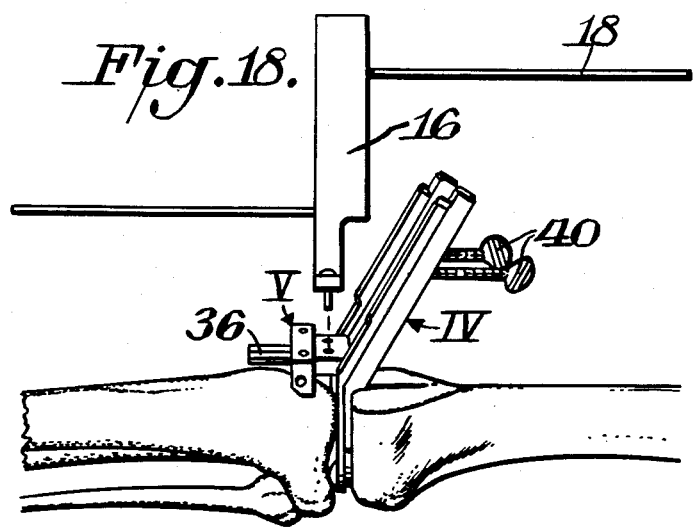

The femoral spacer/tensor jig IV and transverse tibial cutting jig V are now assembled and positioned. The mortise cut out 34 in the transverse tibial cutting jig V is slipped over the tongue 36 of the femoral spacer/tensor jig and slid as far proximally as it will go (FIG. 17). Following insertion of the jig's studs into the femoral fixation holes, the leg is brought into full extension. A folded towel or sheet is placed behind the knee to prevent inadvertent hyperextension at this stage of the procedure. Next the axial alignment guide 16 with both its femoral and tibial alignment pins in place is positioned into the femoral spacer/tensor jig IV (FIG. 18).

Axial And Rotational Alignment

To achieve correct tibial axial alignment prior to making the transverse tibial cut, longitudinal traction and manipulation are applied from the foot. The goal is to bring the center of the ankle joint directly under the distal dip of the alignment pin. This alignment will produce a slight tibial angle of 2.5° (A, FIG. 19). Anatomically, the centers of the ankle joints are closer together than the centers of the knee joints. Overall leg alignment will still be in valgus. Correct extension alignment is achieved when the tibial shaft parallels the alignment pin when viewed from the side. Rotational alignment is correct when the medial malleolus is approximately 30° anterior to the lateral malleolus in the coronal plane (B, FIG. 19).

If correct axial alignment cannot be achieved at this point with the jig IV in place, then one of the special techniques for dealing with the severe deformity will have to be employed. The jig V cannot be locked onto the tibia until correct alignment is achieved.

Soft Tissue/Joint Tension/Alignment

Soft tissue stability is established following initial manual tibial axial alignment. Each side of the femoral spacer/tensor jig IV has expandable arms 38 which spread when its appropriate thumb screw 40 is tightened (FIG. 20). The tensor arms are extended to stabilize the joint in the correct alignment. Do not overtighten the femoral spacer/tensor jig IV. The transverse tibial cutting jig V, pushed as far proximally as it will go ensures that only the minimal amount of the tibial plateaus will be removed. When one plateau is considerably more depressed than the other, the transverse cutting jig should be slid distally so that the plane of the tibial cut will rerove enough bone from the depressed plateau to provide a sufficiently flat surface for seating the tibial prosthesis.

Check Of Overall Alignment

Figure 19A:
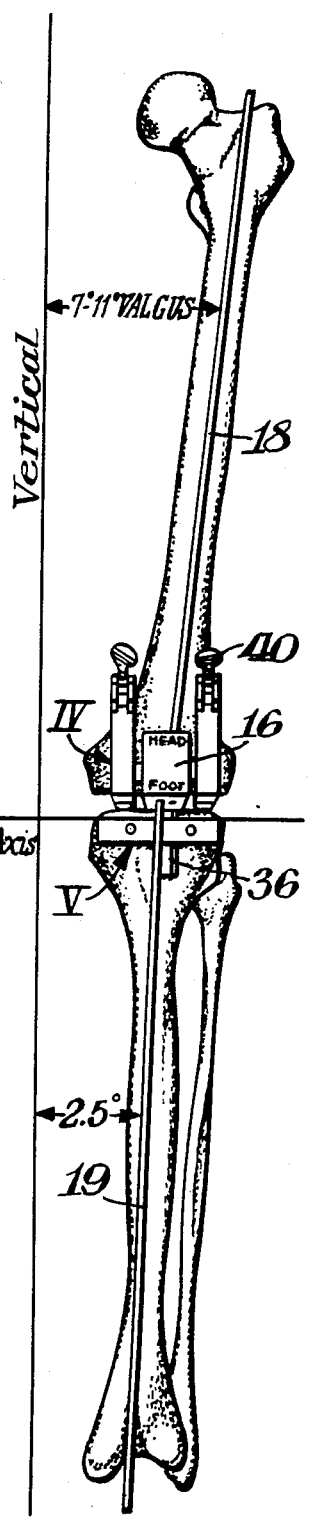
Figure 19B:
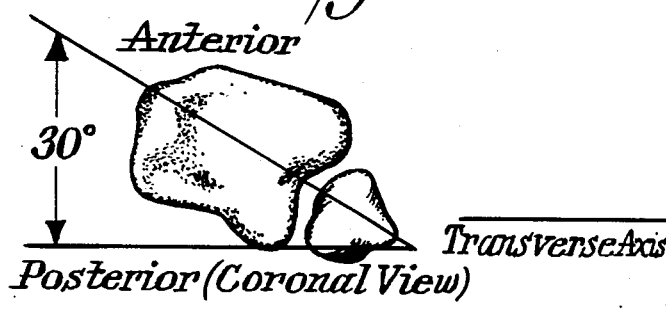

Prior to locking the transverse tibial cutting jig V in place, overall lower limb alignment should be checked. For correct alignment, the femoral alignment pin 18 will parallel the femoral shaft in both the anterior and lateral planes. The tibial alignment pin 19 will extend from the center of the knee to the center of the ankle and be parallel to the tibial shaft, in the lateral plane. Rotation is correct when the medial malleolus is approximately 30° anterior to the lateral malleolus (FIG. 19).

The Transverse Tibial Cut

While still under visual control of the axial alignment guide pins 18, 19, the transverse tibial cutting jig V is locked in place by drilling two ⅛ inch pins through the appropriate holes in the jig (FIG. 21). The alignment guide 16 is now removed and tension is removed from the jig IV by loosening the thumb screws 40. As the knee is flexed to 90°, the femoral spacer/tensor jig IV will pull out of its anchoring holes in the femur. The jig IV is then slipped proximally, disengaging it from the tibial cutting jig V (FIG. 22). The transverse tibial plateau cut is then made by resting the saw blade flush against the broad flat surface of the cutting jig V (FIG. 23). The cut is made as deeply as the saw blade will allow, while care is taken to protect collateral ligaments. Once again, following the initial cut of the oscillating saw blade should be run back and forth across the flat surface of the transverse cutting jig to shave off any prominent bone that may be left posteriorly due to sciving of the saw blade in sclerotic bone. The jig V is then slipped off the locking pins and the cut is completed, making sure that the posterior rims of the plateaus are level with the plane of the transverse cut. Additional care should be taken to preserve the posterior cruciate ligament. Since the transverse tibial cut is made parallel to the ground for optimal stress distribution as the prosthesis bone interface and because the normal tibial plateau slopes 7° to 10° posteriorly, more bone will be removed anteriorly than posteriorly.

Femoral Chamfer Cuts

The femoral chamfer cutting jig VI is inserted then into the femoral fixation holes. With the saw blade flush against the jig's cutting planes 42, the anterior and posterior cuts are made (FIG. 24). As with other cutting jigs, it is important to maintain the saw blade perfectly flush with the cutting surfaces 42 of the jig to assure precise cuts, otherwise the femoral component will not fully seat.

Figure 25:
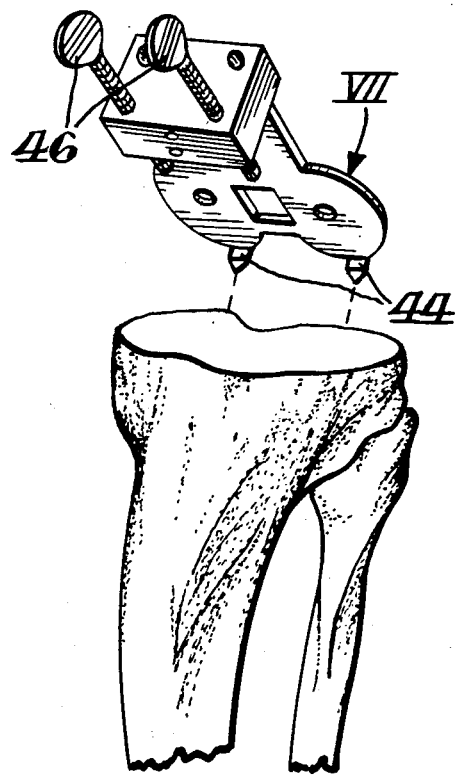
Figure 26:
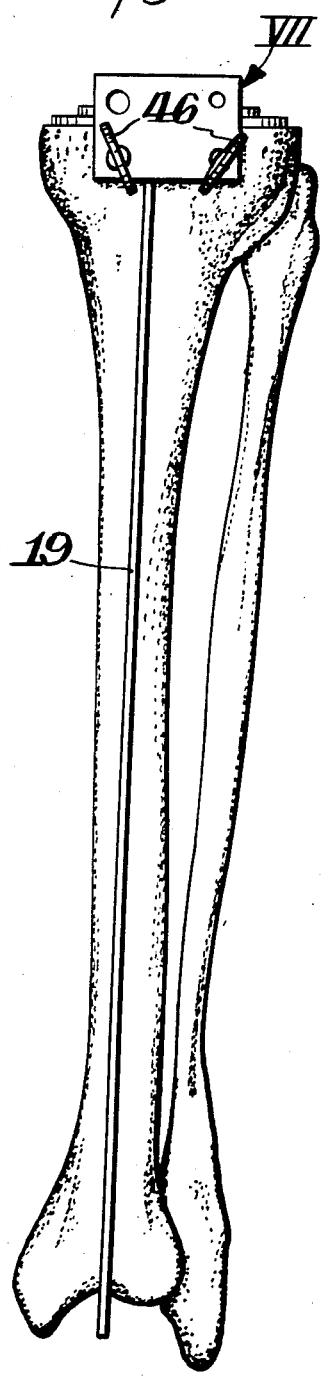

Tibial Component Rotational, Medial-Lateral And Anterior-Posterior Alignment The knee is extended and traction is applied from the foot to open the joint space. The posterior tabs of the appropriate sized tibial positioning/fixation jigs VII are hooked behind the cut proximal tibia (FIG. 25). The two posterior tabs 44 of the jig position behind the posterior rims of the tibial plateau, assuring correct posterior position of the tibial prosthesis. The knee is then flexed and the jig VII is centrally positioned. Since the posterior margins of the tibial plateaus are nearly parallel to the transverse axis of the tibia, the posterior tabs 44 will position the jig in correct rotation. Rotational and medial-lateral positioning are checked by slipping an axial alignment guide pin 19 through the appropriate right or left alignment hole in the anterior flange of the jig. The two anterior thumb screws 46 of the jig are then lightly tightened, securing the jig in place. If alignment is correct, the distal tip of the alignment pin should center over the ankle joint with the medial malleolus 30° anterior to the lateral malleolus (FIG. 26). If this is not the case, the jig is manipulated into proper alignment. Rotational malalignment tends to be toward external rotation of the tibia.

Figure 27:
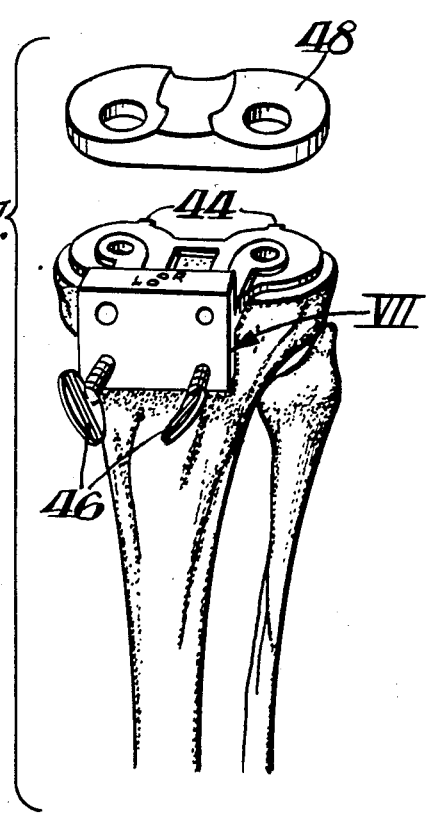

An appropriate size tibial trial prosthesis 48 is inserted onto the jig (FIG. 27). The trial femoral prosthesis is then positioned onto the femur.

Initial Trial Reduction

Figure 28:
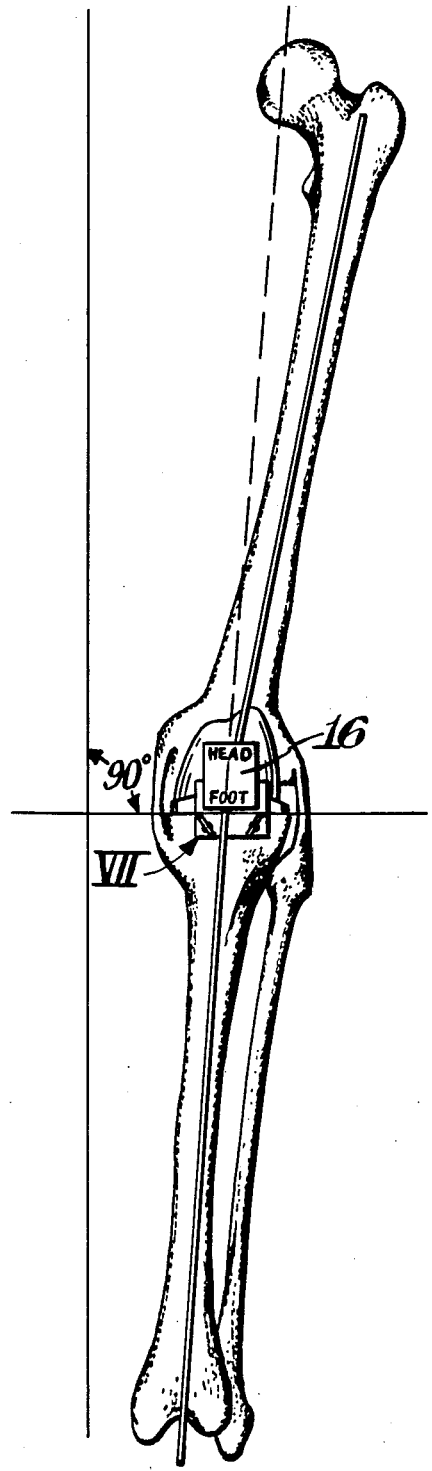
Figure 29:
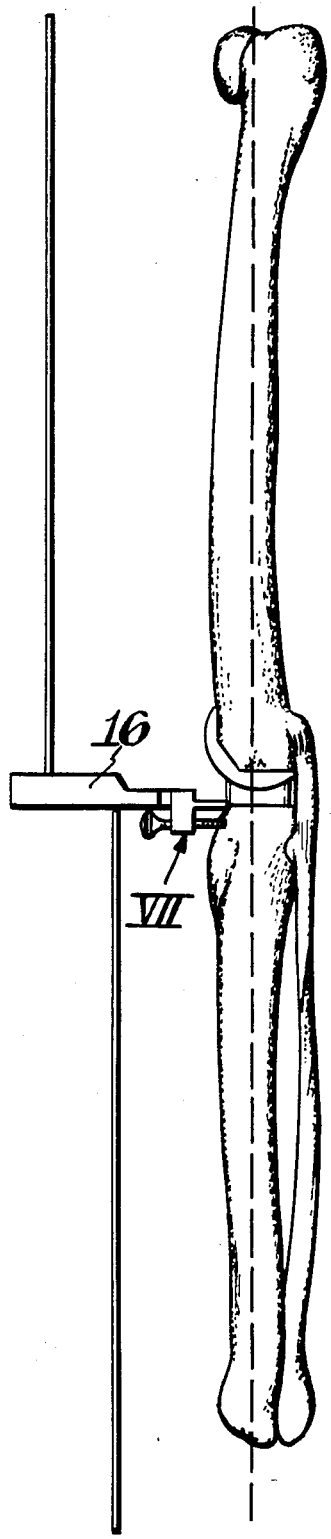

Range of motion and stability are now tested. If the joint is too lax, the next thickest tibial trial is slipped onto the tibial positioning/fixation jig VII. Once flexion, rotation and stability are satisfactory, the overall alignment is checked in full extension (FIGS. 28 and 29). The alignment guide is removed, and the knee is flexed to 90°. Next, the femoral trial and tibial spacer are removed. The thickness marked on the tibial trial spacer indicates the thickness of the prosthesis to be implanted.

Final Tibial Preparation

When the stemmed tibial prosthesis is being used, the window 50 in the jig VII is used, as a cutting guide. A ½ inch osteotome 52 is used to prepare the fixation slot while the jig is still locked onto the proximal tibia (FIG. 30).

Figure 30A:
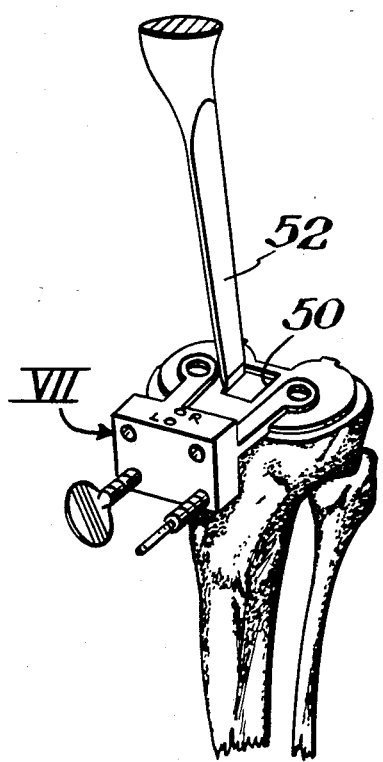
Figure 30B:
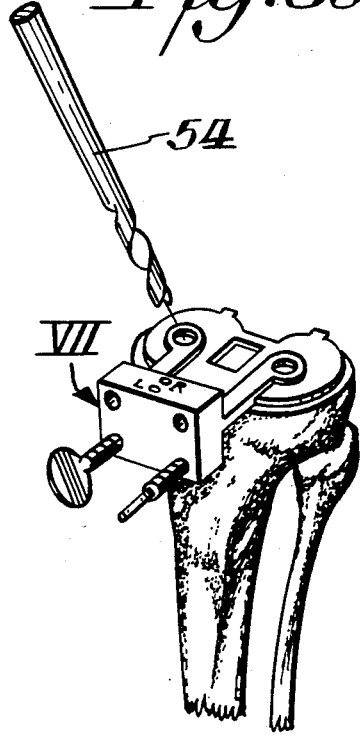
Figure 49:
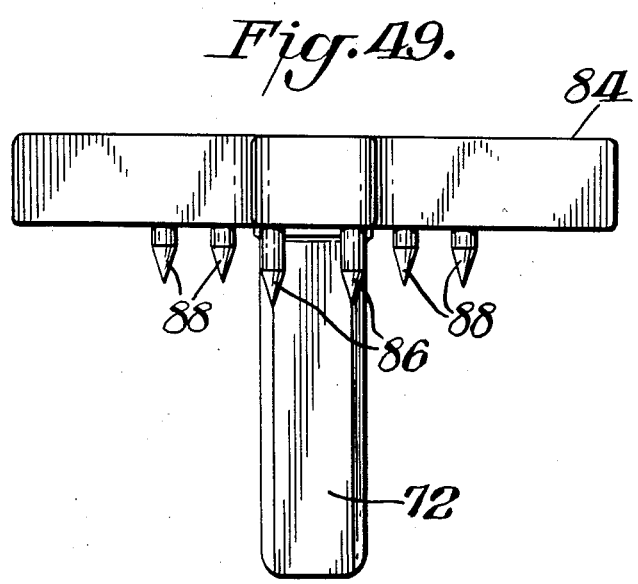
Figure 50:
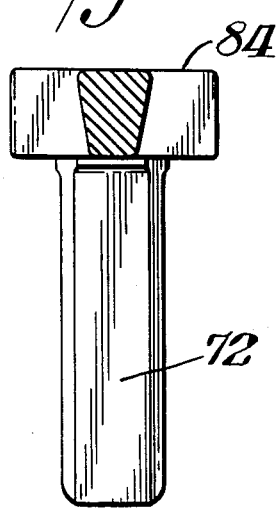
FIG. 50 is a cross-sectional view taken through FIG. 48 along the line 50—50.
Figure 58:
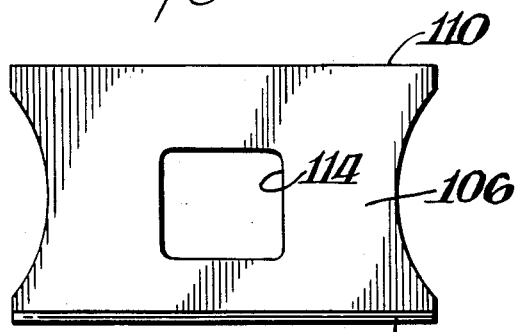
FIGS. 57-61 are top, front, rear, bottom and side views, respectively, of the transverse femoral cutting jig shown in FIGS. 15-16.
Figure 57:
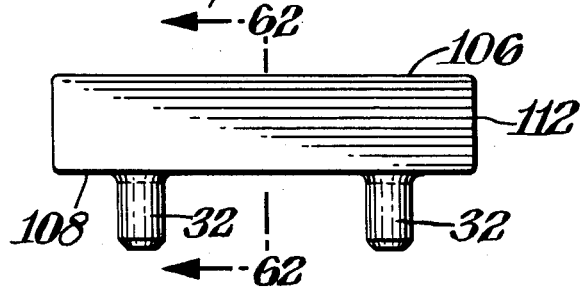
Figure 61:
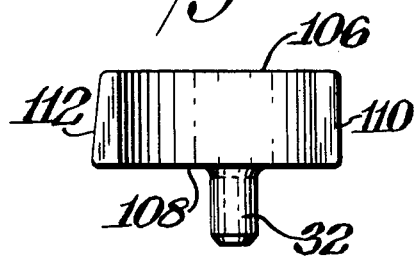
Figure 59:
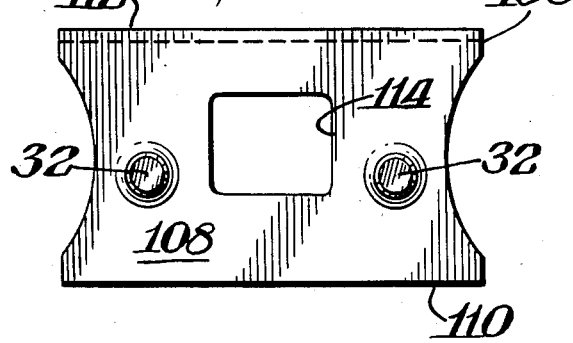
Figure 60:
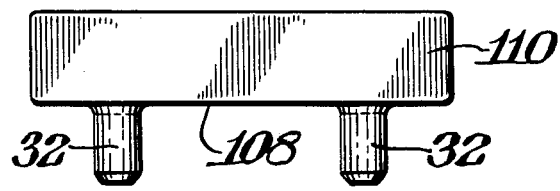
Figure 62:
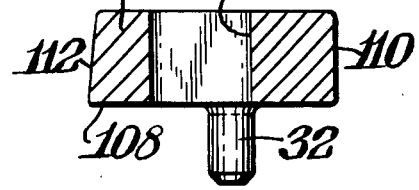
FIG. 62 is a cross-sectional view taken through FIG. 57 along the line 62—62.
Figure 77:
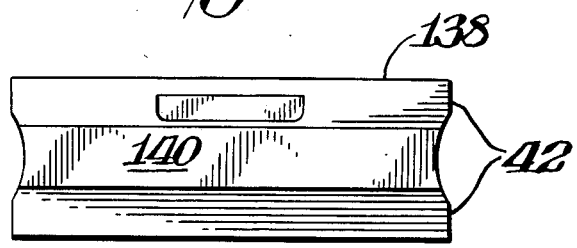
FIGS. 76-80 are bottom, front, rear, top and end views, respectively, of the femoral chamfer cutting jig shown in FIG. 24.
Figure 76:
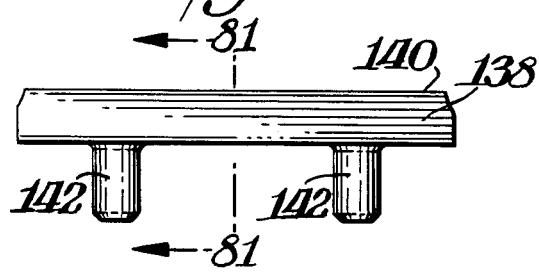
Figure 80:
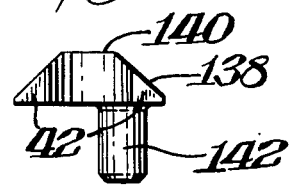
Figure 78:
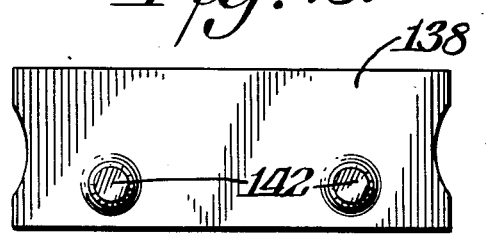
Figure 79:
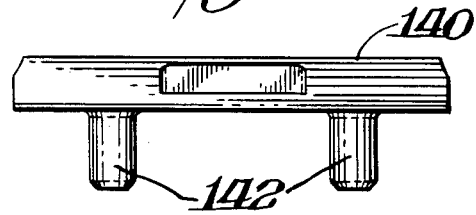
Figure 81:
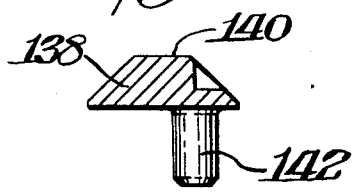
FIG. 81 is a cross-sectional view taken through FIG. 76 along the line 81—81.
Figure 83:
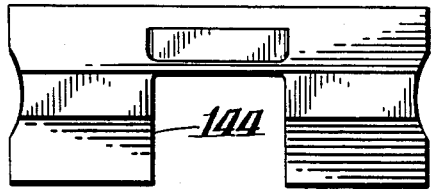
FIGS. 82-86 are bottom, front, rear, top and end views, respectively, of a modified form of femoral chamfer cutting jig.
Figure 82:
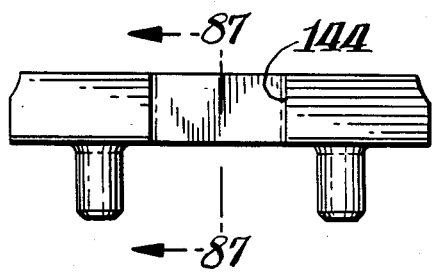
Figure 86:
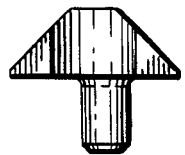
Figure 84:
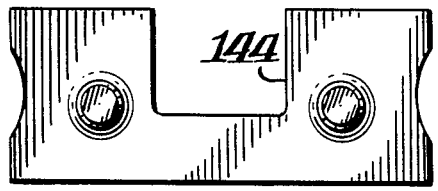
Figure 85:
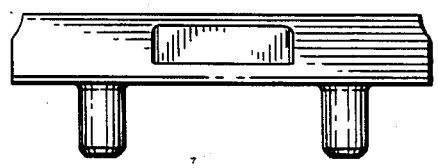
Figure 87:
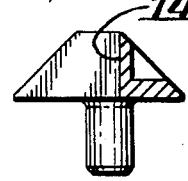
FIG. 87 is a cross-sectional view taken through FIG. 82 along the line 87—87.

For the aforenoted prosthesis resurfacing tibial prosthesis which uses medial and lateral fixation studs, a 5/16 inch drill 54 is used to make the stud holes through the drill guides in the jig VII (FIG. 30). With fixation peg or stud holes completed, the jig is removed. A final check of the joint is made for posterior loose bodies, and soft tissue debridement is completed.

Instruments

FIGS. 31-94 illustrate in full scale various instruments used in accordance with this invention.

FIGS. 31-35 illustrate the distal femoral cutting jig IA which is used for achieving axial alignment when used with the axial adjustment guide 16. Distal femoral cuts are made when jig IA is used with cut jig IB. As indicated therein, the upper surface of the central portion 56 of jig IA has attached thereto a pair of lateral handles 22, 22 while a medial handle 20 also extends from the front face of central section 56. A positioning pin 58 is disposed on the rear face of central section 56 as previously described. Attaching means are provided on the upper surface of the central section 56 for selective attachment of the pin holder alignment guide 16. The attaching means is in the form of a pair of holes 60, 62 which are of different diameter corresponding to the different diameter locking pins 64, 66 (FIG. 37) of the pin holder 16. In this manner there is assurance that the pin holder can be mounted in only the correct position.

The rear surface of central section 56 also includes a pair of short alignment pins 68 as previously described.

A vertical cut-out 70 extends completely through central section 56 for receiving the tongue 72 (FIG. 45) of the distal femur cutting jig IB. An adjustable locking screw 74 is movable into cut-out 70 to lock tongue 72 in place.

FIGS. 36-44 illustrate the details of pin holder 16 which is used with guide pins 18, 19 (FIG. 19) to assure correct axial alignment throughout the surgical procedure. Pin holder 16 is in the form of an elongated bar and includes bifurcated pins 64, 66 to complement the holes 60, 62 in jig IA. The lower portion of pin holder 16 is provided with a pair of mirror image tibial holes 76, 76 for selectively receiving tibial alignment pin 19. The holes are angled oppositely each other, as previously described, with one holder being for the right knee and the other being for the left knee. Similarly, three sets of holes 78, 80, 82 are provided for the femoral alignment pin 18. The holes are disposed at the most likely angle required such as 7°, 9° and 11° with one set being for the right knee and the other for the left knee.

FIGS. 45-50 illustrate the details of distal femoral cutting jig IB which is in the form of a plate or bar having a downwardly extending tongue 72 with non-symmetric cross-section of complementary size and shape to fit within the mortise cut-out 70 of jig IA. Jig IB is used for cutting the distal femoral condyles. Plate 84 includes a pair of femoral securing pins 86 for attachment to the femur with two pairs of positioning pins 88 spaced inwardly thereof. The upper surface of plate 84 is also provided with a pair of non-identical holes 90, 92 for receiving the locking pins 64, 66 of pin holder 16. Plate 84 is also provided with a generally vertical guide surface 94 on each wing portion thereof to act as a saw cutting guide (see FIG. 13). A pair of vertical holes 96 are provided in plate 84.

FIGS. 51–56 illustrate the femoral cutting jig II which is used to determine the rotational, medial-lateral and anterior-posterior orientation of the femoral component and allows drilling of holes for prosthesis fixation stud. As shown therein, jig II is in the form of a generally vertical plate 98 having a flat inner surface 100. A pair of posterior skids 24 extend outwardly from inner surface 100 at the lower portion thereof. A pair of drill holes 26 extend through plate 98 as previously described. If the posterior condyles are intact, a hole may be drilled therein through the aid of one of the drill holes 102, 102 with holes 102, 102 being inclined for the right and left knee. Plate 98 also includes a pair of positioning oins 104 on its inner surface 100.

FIGS. 57–62 illustrate the anterior-posterior cutting jig III. As indicated therein, jig III is in the form of a bar or plate 106 which has a flat vertical surface 108. A pair of distal femoral fixation pins 32 extend from surface 108. A generally horizontal lower cutting guide surface 110 is also provided as well as an upwardly inclined cutting guide surface 112. A cut-out 114 is located centrally of bar 106. Preferably jig III would come in small, medium and large sizes.

FIGS. 63–68 illustrate the details of femoral spacer/tensor jig IV which assembles and positions transverse tibial cutting jig V to determine correct soft tissue balance and tibial axial and rotational alignment prior to making the transverse tibial cut. Jig IV comprises a pair of spaced fixed legs 116 with each leg having a lower vertical section and an inwardly inclined upper section. A transverse bridge member 118 joins the fixed legs at the junction of the upper and lower sections. A pair of spaced parallel movable legs 38 generally conform in size and shape to fixed legs 116 and are hingedly mounted at their ends thereof by hinge connection 102 to their respective movable legs. Adjusting means in the form of bolts or thumb screws 40 are threadably engaged with and extend through fixed legs 116 into contact with movable legs 38 for controlling the spacing or relative positioning of the respective sets of legs. A pair of studs 126 are provided at the lower portion of legs 116 while rounded contact surfaces 128 extend away from movable legs 38. Legs 38 may be thus be moved so that surfaces 128 contact the tibia. Bridge member 118 includes outwardly extending tongue 36 which is of non-symmetrical cross section for complementary engagement with mortise cut-out 34 in jig V (FIG. 17). Jig V could then slide in or out on tongue 36 to adjust for the length of cut.

FIGS. 69–75 illustrate transverse tibial cutting jig V which is in the form of a bar 130 having a flat upper cutting guide surface 132 and cut-out 34 for receiving tongue 36 of jig IV. A locking screw 134 is movable into cut-out 34 to lock tongue 36 in place. A pair of vertical drill holes 136 also extend through bar 130.

FIGS. 76–81 show one form of femoral chamfer cutting jig VI which is in the form of a bar 138 having its front face formed in three sections which include a pair of inclined upper and lower cutting guide surfaces 42 extending to the upoer edge and lower edge of bar 138. The intermediate surface 140 is generally vertical. A pair of positioning studs 142 are provided to extend into the same medial alignment holes which are utilized by various other jigs.

FIGS. 82–87 show a modified form of jig VI wherein a condylar cut-out 144 is provided in the lower guide surface. Preferably jig VI would come in five different sizes varying in size of the cut-out 144 and/or being sized small, medium or large.

FIGS. 88–94 illustrate the tibial positioning/fixation jig VII. Jig VII generally includes a plate 146 having a lower planar surface 148 from which extend a pair parallel tabs 44. An osteotome cut-out or window 50 is provided in the central portion thereof with an inclined drill hole 150 on each side of cut-out 50. A block 152 is connected to plate 146. A pair of vertical alignment holes 154 which are inclined for the right and left knee extend through block 152. Additionally thumb screws 46 are threadedly mounted into and extend through block 152 while a pair of non-identical holes 156, 158 are provided in block 152 for receiving the locking pins 64, 66 of holder 16.

What is claimed is:

1. In a method of preparing a knee for prosthetic knee implantation wherein bone cuts are made to juxtaposed portions of the femur and tibia to generally conform those surfaces for having a prosthetic knee secured thereto, the improvement being initially mounting a distal femoral cutting jig to the distal end of the femur, securing an alignment rod to the distal femoral cutting jig to establish proper varus-valgus and flexion-extension alignment therewith, locking the distal femoral cutting jig to the femur after proper alignment therewith, cutting the distal end of the femur for the transverse distal femoral cut through use of a guide surface on the distal femoral cutting jig, and making the remaining bone cuts of the femur and tibia.

2. In the method of claim 1, including mounting a femoral drill jig to the distal end of the femur for determining the medial/lateral and rotational positioning of the femoral component of the prosthesis, using the femoral drill jig for making positioning holes in the distal end of the femur, removing the femoral drill jig, mounting an anterior-posterior femoral cutting jig to the distal end of the femur with the aid of locking members secured to the positioning holes, making the anterior and posterior femoral bone cuts by using guide surfaces on the anterior-posterior femoral cutting jig.

3. In the rethod of claim 2, including mounting a femoral spacer/tensor jig to the distal end of the femur and mounting a tibial cutting jig to the femoral spacer/tensor jig, mounting an axial alignment guide to the femoral spacer/tensor jig, positioning an alignment guide pin to the axial alignment guide for alignment with the center of the ankle joint, and transversely cutting the tibial bone with the aid of a guide surface on the transverse tibial cutting jig.

4. In the method of claim 3, including mounting a chamfer cutting jig to the distal end of the femur, and making anterior and posterior cuts of the femur with the aid of guide surfaces on the femoral chamfer cutting jig.

5. In the method of claim 4, including mounting a tibial positioning/fixation jig to the tibia, and checking the rotational and medial-lateral position of the tibia by the aid of an axial alignment guide pin positioned in the tibial positioning/fixation jig.

6. In the method of claim 1, including mounting a femoral spacer/tensor jig to the distal end of the femur and mounting a tibial cutting jig to the femoral spacer/tensor jig, mounting an axial alignment guide to the femoral spacer/tensor jig, positioning an alignment guide pin to the axial alignment guide for alignment with the center of the ankle joint, and transversely cutting the tibial bone with the aid of a guide surface on the transverse tibial cutting jig.

7. In the method of claim 1, including mounting a chamfer cutting jig to the distal end of the femur, and making anterior and posterior cuts of the femur with the aid of guide surfaces on the femoral chamfer cutting jig.

8. In the method of claim 1, including mounting a tibial positioning/fixation jig to the tibia, and checking the rotation and medial-lateral position of the tibia by the aid of an axial alignment guide pin positioned in the tibial positioning/fixation jig.

* * * * *

UNITED STATES PATENT AND TRADEMARK OFFICE
CERTIFICATE OF CORRECTION

PATENT NO. : 4,646,729

DATED : March 3, 1987

INVENTOR(S) : Robert V. Kenna, et al.

It is certified that error appears in the above-identified patent and that said Letters Patent is hereby corrected as shown below:

Cover page after [22] insert --

Related U.S. Application Data
[63] Continuation of Serial No. 350,013, filed February 18, 1982, now abandoned --

Col. 1, after the title insert --

CROSS REFERENCE TO RELATED APPLICATION
This application is a continuation of application Serial No. 350,013, filed February 18, 1982, now abandoned.

Signed and Sealed this

First Day of September, 1987

Attest:

Attesting Officer

DONALD J. QUIGG

Commissioner of Patents and Trademarks